United States Patent
Navia et al.

(10) Patent No.: US 8,105,375 B2
(45) Date of Patent: Jan. 31, 2012

(54) METHOD FOR IMPLANTING A CARDIOVASCULAR VALVE

(75) Inventors: Jose Luis Navia, Shaker Heights, OH (US); Ji-Feng Chen, Lakewood, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 837 days.

(21) Appl. No.: 12/016,168

(22) Filed: Jan. 17, 2008

(65) Prior Publication Data

US 2008/0177381 A1     Jul. 24, 2008

Related U.S. Application Data

(60) Provisional application No. 60/881,244, filed on Jan. 19, 2007.

(51) Int. Cl.
*A61F 2/24* (2006.01)

(52) U.S. Cl. ........ 623/2.1; 623/2.11; 623/2.13; 623/2.14

(58) Field of Classification Search .......... 623/2.1–2.18, 623/1.23–1.26, 23.68
See application file for complete search history.

(56) References Cited

U.S. PATENT DOCUMENTS

| | | | |
|---|---|---|---|
| 5,156,621 A | 10/1992 | Navia et al. | |
| 5,336,616 A * | 8/1994 | Livesey et al. | 435/395 |
| 5,411,552 A | 5/1995 | Andersen et al. | |
| 5,782,914 A * | 7/1998 | Schankereli | 435/325 |
| 6,126,686 A | 10/2000 | Badylak et al. | |
| 6,425,916 B1 | 7/2002 | Garrison et al. | |
| 6,458,156 B1 * | 10/2002 | Wan et al. | 623/2.14 |
| 6,534,004 B2 * | 3/2003 | Chen et al. | 422/40 |
| 6,547,827 B2 | 4/2003 | Carpentier et al. | |
| 6,561,970 B1 | 5/2003 | Carpentier et al. | |
| 6,582,462 B1 | 6/2003 | Andersen et al. | |
| 6,630,001 B2 * | 10/2003 | Duran et al. | 623/23.72 |
| 6,641,611 B2 | 11/2003 | Jayaraman | |
| 6,878,168 B2 * | 4/2005 | Carpentier et al. | 8/94.11 |
| 6,969,400 B2 * | 11/2005 | Rhee et al. | 623/11.11 |
| 7,125,418 B2 * | 10/2006 | Duran et al. | 623/1.24 |
| 7,578,842 B2 * | 8/2009 | Woo | 623/2.1 |
| 7,618,446 B2 | 11/2009 | Andersen et al. | |
| 7,648,527 B2 | 1/2010 | Agnew | |
| 7,717,951 B2 * | 5/2010 | Flagle et al. | 623/1.23 |
| 2001/0039450 A1 * | 11/2001 | Pavcnik et al. | 623/1.24 |

(Continued)

FOREIGN PATENT DOCUMENTS

WO    WO 2008/063338 A2    5/2008

*Primary Examiner* — Corrine M McDermott
*Assistant Examiner* — Dianne Dornbusch
(74) *Attorney, Agent, or Firm* — Orrick, Herrington & Sutcliffe LLP

(57) ABSTRACT

A method is provided for implanting a valve having at least one valve leaflet within the cardiovascular system of a subject. One step of the method includes preparing a substantially dehydrated bioprosthetic valve and then providing an expandable support member having oppositely disposed first and second ends and a main body portion extending between the ends. Next, the substantially dehydrated bioprosthetic valve is attached to the expandable support member so that the substantially dehydrated bioprosthetic valve is operably secured within the main body portion of the expandable support member. The expandable support member is then crimped into a compressed configuration and placed at a desired location within the cardiovascular system of the subject. Either before or after placement at the desired location, fluid or blood re-hydrates the substantially dehydrated bioprosthetic valve.

22 Claims, 25 Drawing Sheets

U.S. PATENT DOCUMENTS

| | | |
|---|---|---|
| 2002/0133183 A1 | 9/2002 | Lentz et al. |
| 2002/0151958 A1* | 10/2002 | Chuter .................... 623/1.13 |
| 2003/0023303 A1 | 1/2003 | Palmaz et al. |
| 2003/0130729 A1* | 7/2003 | Paniagua et al. ............ 623/2.11 |
| 2003/0181974 A1* | 9/2003 | Xie et al. ................. 623/1.24 |
| 2003/0199963 A1* | 10/2003 | Tower et al. ............... 623/1.11 |
| 2004/0186558 A1* | 9/2004 | Pavcnik et al. ............. 623/1.24 |
| 2004/0243230 A1* | 12/2004 | Navia et al. ............... 623/2.36 |
| 2005/0021136 A1* | 1/2005 | Xie et al. ................. 623/2.14 |
| 2005/0075725 A1* | 4/2005 | Rowe ..................... 623/2.14 |
| 2005/0137682 A1* | 6/2005 | Justino ................... 623/1.24 |
| 2005/0137688 A1 | 6/2005 | Salahich et al. |
| 2005/0148512 A1* | 7/2005 | Hunter et al. ............... 514/12 |
| 2005/0152881 A1* | 7/2005 | Mills et al. ................ 424/93.7 |
| 2005/0171599 A1* | 8/2005 | White .................... 623/1.36 |
| 2005/0216079 A1 | 9/2005 | MaCoviak |
| 2006/0155363 A1* | 7/2006 | LaDuca et al. ............. 623/1.16 |
| 2006/0190074 A1* | 8/2006 | Hill et al. ................. 623/1.23 |
| 2006/0195183 A1 | 8/2006 | Navia et al. |
| 2007/0027460 A1* | 2/2007 | Case et al. ................. 606/151 |
| 2007/0073392 A1* | 3/2007 | Heyninck-Jantz et al. .. 623/2.14 |
| 2007/0100435 A1* | 5/2007 | Case et al. ................ 623/1.24 |
| 2008/0281411 A1 | 11/2008 | Berreklouw |

* cited by examiner

METHOD FOR IMPLANTING A CARDIOVASCULAR VALVE

RELATED APPLICATION

This application claims priority from U.S. provisional patent application Ser. No. 60/881,244, filed on Jan. 19, 2007, the subject matter of which is incorporated herein by reference.

TECHNICAL FIELD

The present invention relates generally to a method for treating and improving the function of cardiovascular valves, and more particularly to a method for implanting a cardiovascular valve within the cardiovascular system of a subject.

BACKGROUND OF THE INVENTION

A number of implantable bioprosthetic devices are currently being used for treating patients with cardiovascular diseases and defects. Such implantable devices are useful for replacing diseased, damaged, or congenitally malformed components of a patient's cardiovascular system. Thus, damaged or diseased heart valves have been replaced with chemically-fixed, bioprosthetic heart valves prepared from tissues of porcine or bovine origin. Similarly, regions of damaged or diseased blood vessels may also be replaced with bioprosthetic vessels prepared from bovine tissues.

Typically, the animal tissues used to form implantable devices are chemically cross-linked with agents, especially those animal tissue components that come into direct contact with the blood of a patient, and then chemically sterilized and preserved in a chemical solution. Such treatment is necessary to prevent rejection of the implanted bioprosthetic device by the recipient. Such treatment also stabilizes the protein components of the animal tissue, thus making them more resistant to degradation by proteolytic enzymes.

The use of chemically-treated implantable bioprosthetic devices presents several drawbacks, however. For example, the presence of chemically cross-linked/preserved agents, such as glutaraldehyde, presents an environmental hazard to the operating room personnel who are exposed to these chemicals as well as personnel involved in transporting such tissues. Consequently, preparation of chemically-treated devices in the operating room is a cumbersome and time consuming process as the chemical agents must be rinsed thoroughly off of the devices and then carefully crimped and loaded into a delivery catheter.

SUMMARY OF THE INVENTION

In one aspect of the present invention, a method is provided for implanting a valve having at least one valve leaflet within the cardiovascular system of a subject. One step of the method comprises preparing a substantially dehydrated bioprosthetic valve and providing an expandable support member having oppositely disposed first and second ends and a main body portion extending between the ends. The substantially dehydrated bioprosthetic valve is attached to the expandable support member so that the substantially dehydrated bioprosthetic valve is operably secured within the main body portion of the expandable support member. The expandable support member is then crimped into a compressed configuration and placed at a desired location within the cardiovascular system of the subject.

In another aspect of the present invention, a method is provided for implanting a valve having at least one valve leaflet within the cardiovascular system of a subject. One step of the method comprises preparing a substantially dehydrated bioprosthetic valve and providing an expandable support member having oppositely disposed first and second ends and a main body portion extending between the ends. The substantially dehydrated bioprosthetic valve is attached to the expandable support member so that the substantially dehydrated bioprosthetic valve is operably secured within the main body portion of the expandable support member. The expandable support member is next crimped into a compressed configuration and exposed to a re-hydrating fluid. The substantially dehydrated bioprosthetic valve is then placed at a desired location within the cardiovascular system of the subject.

In another aspect of the present invention, a method is provided for implanting a valve having at least one valve leaflet within the cardiovascular system of a subject. One step of the method comprises preparing a substantially dehydrated bioprosthetic valve and providing an expandable support member having oppositely disposed first and second ends and a main body portion extending between the ends. The substantially dehydrated bioprosthetic valve is attached to the expandable support member so that the substantially dehydrated bioprosthetic valve is operably secured within the main body portion of the expandable support member. The substantially dehydrated bioprosthetic valve is next exposed to a re-hydrating fluid. The expandable support member is then crimped into a compressed configuration and placed at a desired location within the cardiovascular system of the subject.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
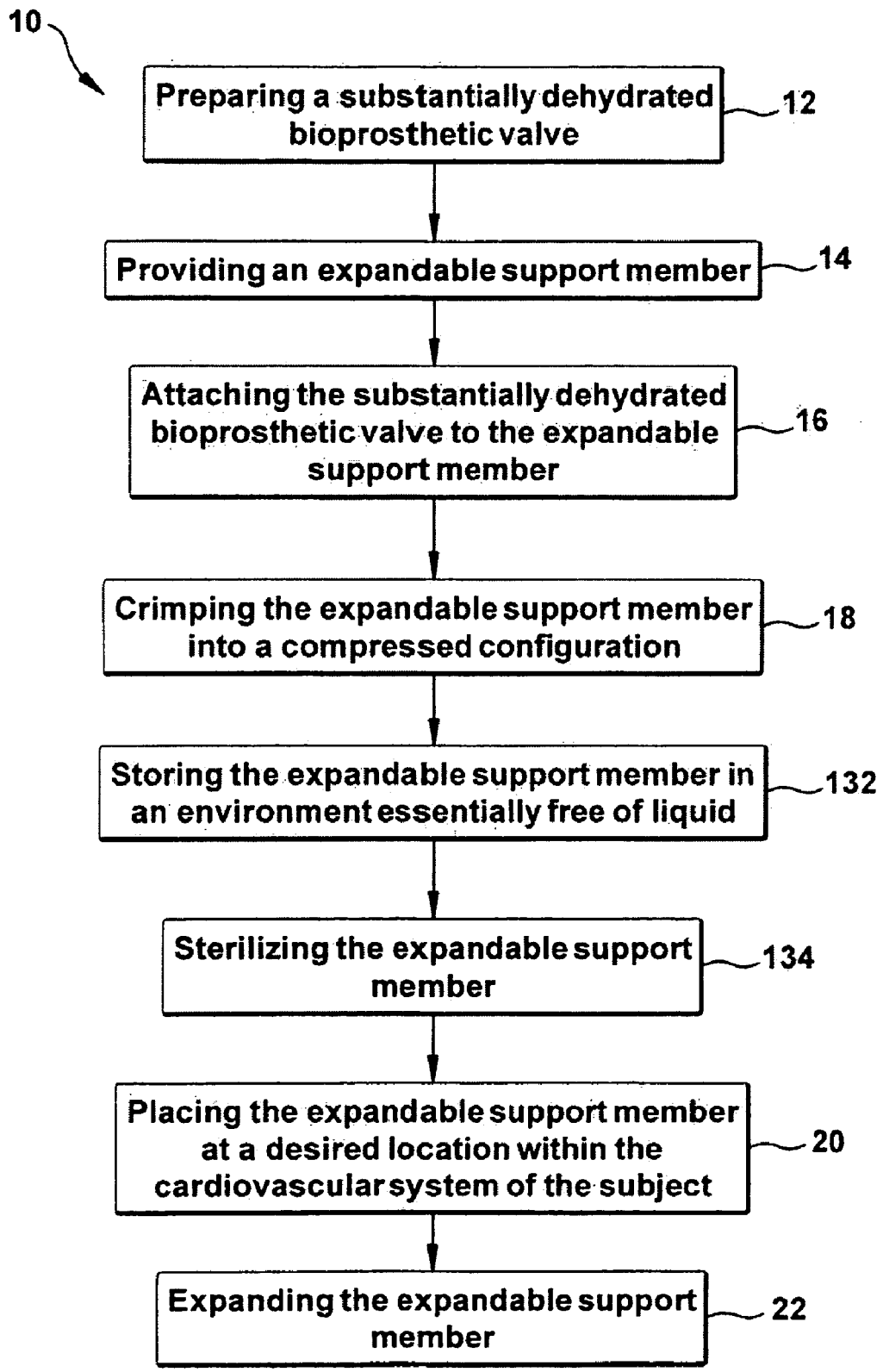
FIG. 1 is a flow diagram illustrating a method for implanting a valve having at least one leaflet within the cardiovascular system of the subject in accordance with the present invention.
Figure 3:
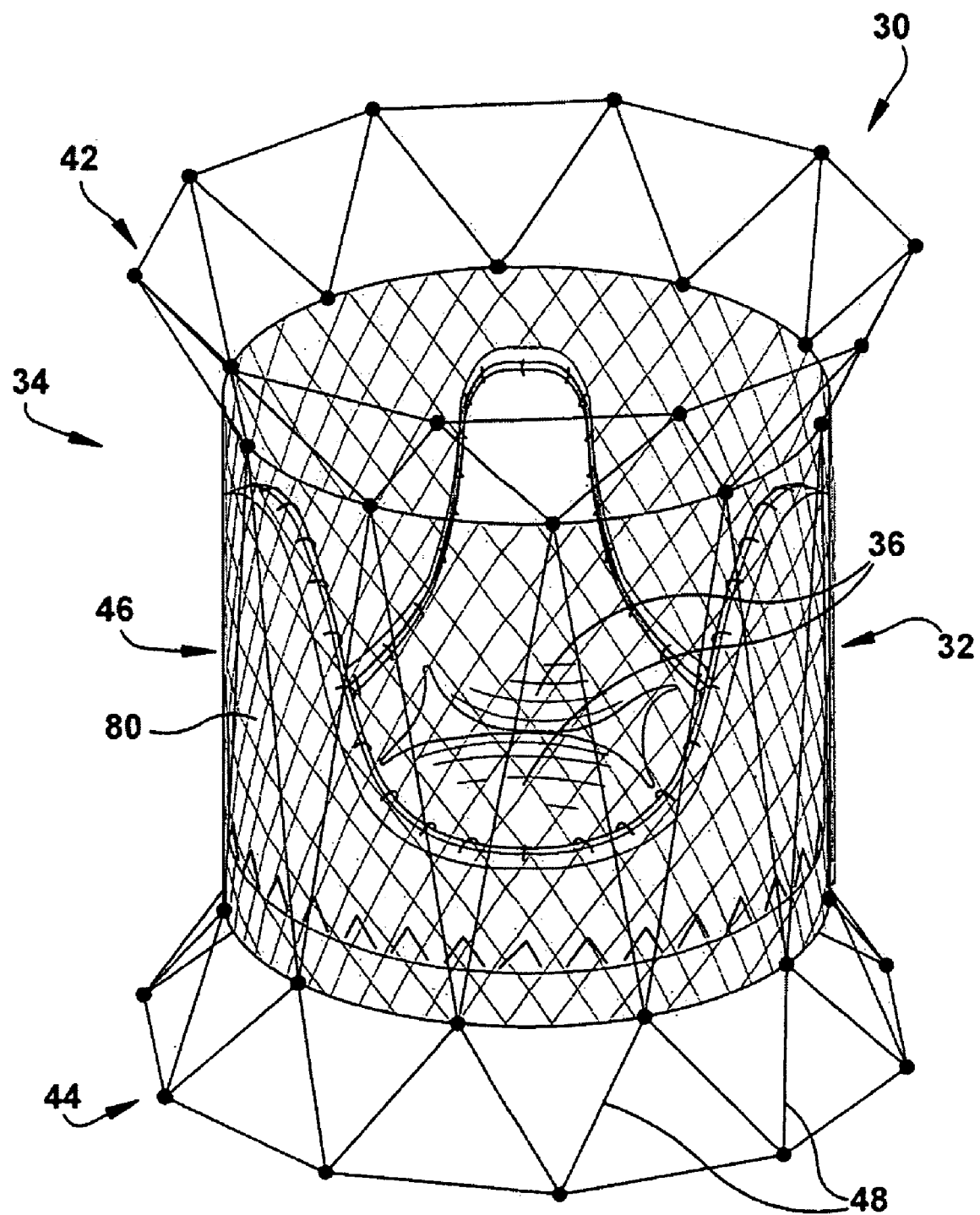
FIG. 3 is a perspective view of a substantially dehydrated bioprosthetic valve securely attached to an expandable support member in an expanded configuration.

The present invention relates generally to a method for treating and improving the function of cardiovascular valves, and more particularly to a method for implanting a cardiovascular valve within the cardiovascular system of a subject. As used herein, the term "cardiovascular system" refers to a bodily system consisting of the heart, blood vessels, and blood that circulates blood throughout the body, delivers nutrients and other essential materials to cells, and removes waste products. As representative of the present invention, FIG. 1 illustrates a method 10 for implanting a valve 30 (FIG. 3) having at least one valve leaflet 36 within the cardiovascular system of a subject, wherein the valve comprises a substantially dehydrated bioprosthetic valve 32 securely attached to an expandable support member 34. Advantageously, the method 10 (FIG. 1) of the present invention minimizes, if not eliminates, the possibility of introducing aldehydes into the blood stream of the subject while also preserving the functional properties of the valve 30 (FIG. 3). The present method 10 also avoids the problems associated with exposing manufacturing or operating room personnel to the fumes given off by aldehyde-containing solutions, in turn reducing the risk of damaging the valve 30 and the amount of time spent in the operating room preparing the valve for implantation.

Figure 2:
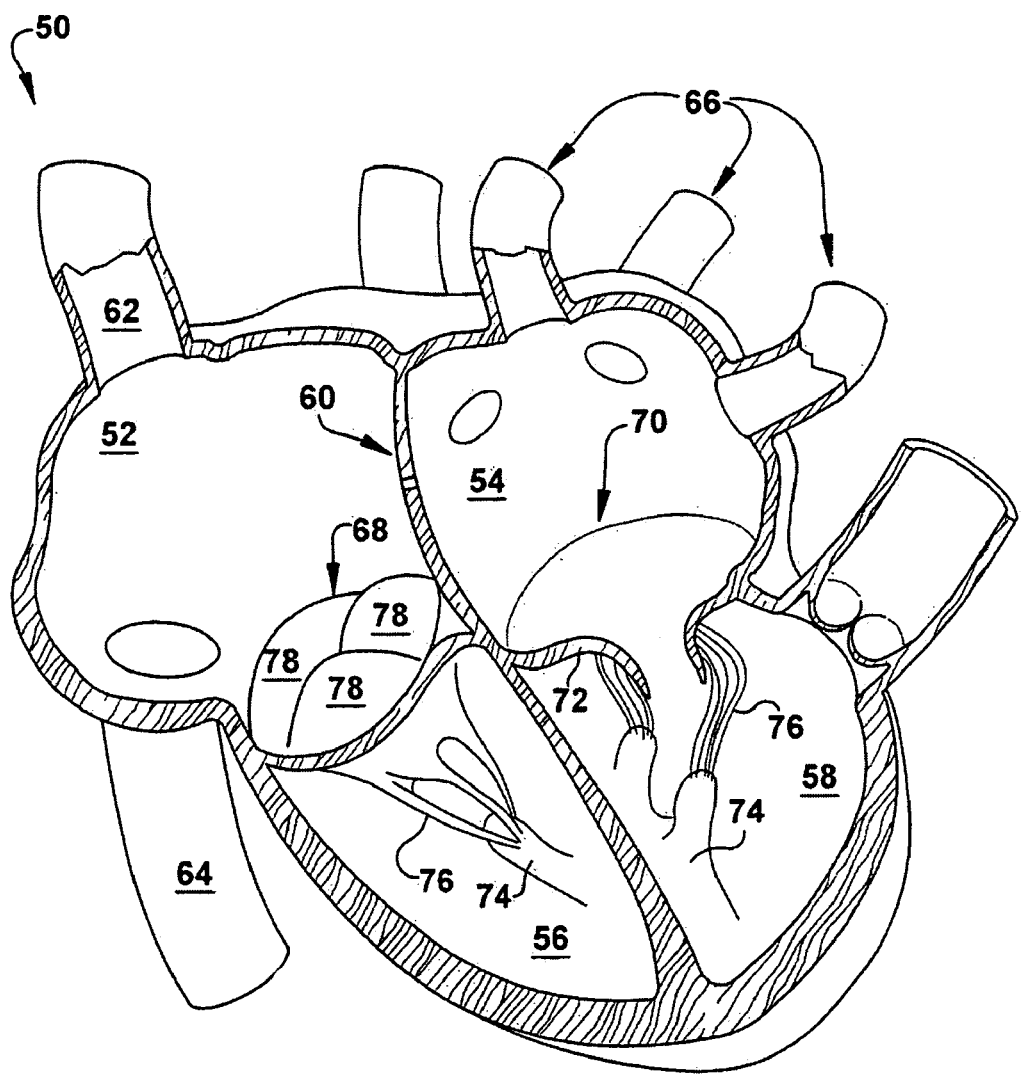
FIG. 2 is a cross-sectional schematic view of a human heart.

FIG. 2 schematically illustrates a human heart 50. The human heart 50 includes four chambers: the right and left atria 52 and 54 and the right and left ventricles 56 and 58. The right and left atria 52 and 54 are divided by the interatrial septum 60. The thin-walled right atrium 52 receives deoxygenated blood from the superior vena cava 62, the inferior vena cava 64, and from the coronary sinus (not shown). The thin-walled left atrium 54 receives oxygenated blood from pulmonary veins 66. The right and left ventricles 56 and 58 pump oxygenated and deoxygenated blood, respectively, throughout the body, and the pocket-like semilunar pulmonary valve (not shown) and the aortic valve (not shown) prevent reflux into the ventricles. Atrial blood is pumped through the atrioventricular orifices, guarded by the tri-leaflet tricuspid valve 68 on the right side of the heart 50 and the bi-leaflet mitral valve 70 on the left side of the heart. The leaflets 72 of the mitral valve 70 are attached to the papillary muscles 74 in the right and left ventricles 56 and 58 by chordae tendineae 76. Similarly, the leaflets 78 of the tricuspid valve 68 are attached to the papillary muscles 74 in the right and left ventricles 56 and 58 by chordae tendineae 76.

In one embodiment of the present invention, a method 10 (FIG. 1) is provided for implanting a valve 30 having at least one valve leaflet 36 within the cardiovascular system of a subject. As used herein, the term "subject" refers to any mammal including, for example, human beings, dogs, cats, horses, and non-human primates. At 12, one step of the method 10 comprises preparing a substantially dehydrated bioprosthetic valve 32 (FIG. 3). The substantially dehydrated bioprosthetic valve 32 is prepared according to the teachings of U.S. Pat. No. 6,534,004, the subject matter of which is hereby incorporated by reference.

Briefly, a tissue component 38 (FIG. 4) is fixed by treating the tissue component with an aqueous solution comprising at least one non-volatile, biocompatible dimensional stabilizer at a concentration, temperature, and for a time sufficient to allow an equilibrium to be reached between the fluids in the interstices of the tissue component and the aqueous solution. As used herein, the term "tissue component" refers to tissue that is dissected from an animal including, for example, muscular tissues, connective tissues, epithelial tissues, or combinations thereof, and tissues or tissue precursors that are formed in animal cell cultures. The tissue component 38 can include, but is not limited to, a heart valve (e.g., a bi- or tri-leaflet valve), peritoneum, pleura, submucosal tissue, dura mater and/or pericardium obtained from non-human animals, such as porcine, equine and/or bovine animals, in addition to human donors (e.g., cadaveric tissue).

As used herein, the term "fixed" when used with reference to the tissue component 38 refers to a tissue component in which the proteins thereof have reduced solubility, antigenicity, and biodegrading properties as compared to the proteins in a native tissue component. The tissue component 38 may be fixed by cross-linking the amine groups of the proteins of the tissue component with an aldehyde, such as glutaraldehyde or formaldehyde, for example.

Dimensional stabilizers include organic molecules that are hydrophilic and that comprise a plurality of carbon atoms attached to a plurality of hydroxyl groups. Examples of dimensional stabilizers include, but are not limited to, water soluble polyhydric alcohols such as glycerol, ethylene glycol, polyethylene glycols, propylene glycol, butylene glycol, sorbitol, mannitol, and pentaerythritol; water soluble carbohydrates such as ribose, maltose, sucrose, fructose, dextrose, dextran, cellulose, and methyl cellulose; pectin; derivatives of glycerol including, for example, glycerol bori-borate and glycerol borate akerite glycerin alternative; and water soluble gums.

At 12, the tissue component 38 is contacted with the aqueous treatment solution for a time and at a temperature sufficient to permit the treatment solution to penetrate into the interstices of the tissue component and achieve an equilibrium between the treatment solution and the fluids in the interstices of the tissue component. The time needed to achieve such equilibrium is directly related to the thickness of the tissue component 38 and to the concentration of the dimensional stabilizer in the solution. Additionally, the time needed to achieve equilibrium is inversely related to the ratio between the volumes of the treatment solution and the tissue component 38 to the rate of mixing of the treatment solution.

After the tissue component 38 has been treated, the tissue component is formed into a substantially dehydrated bioprosthetic valve 32 (FIG. 3) or, alternatively, exposed to ambient air at standard room temperature and humidity. Where the tissue component 38 is exposed to air following treatment, the tissue component may be air dried for a time sufficient to increase the viscosity of the dimensional stabilizer in the solution entrapped within the interstices of the tissue component such that the treated tissue component is essentially free from excess aqueous treatment solution.

Figure 4:
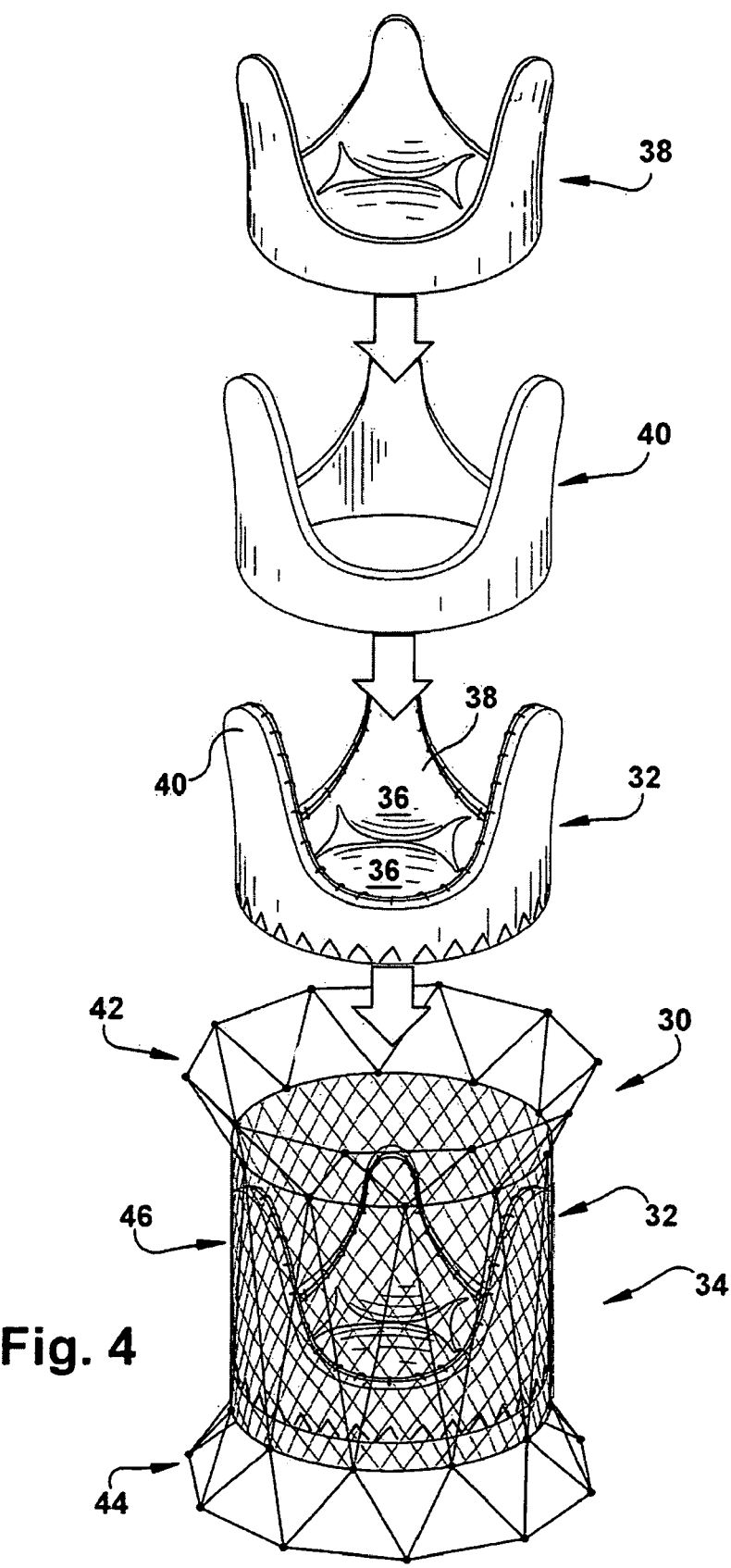
FIG. 4 is a perspective view showing a process for forming the valve shown in FIG. 3.

After preparing the tissue component 38, the substantially dehydrated bioprosthetic valve 32 is formed. As illustrated in FIG. 4, the tissue component 38 is first securely attached to a root component 40. The root component 40 provides both structural support and a substrate for attachment of the tissue component 38. The root component 40 may be made of a scaffolding material, such as a harvested aortic root, for example, or any other suitable scaffolding material, such as biological tissue (e.g., pericardium, peritoneal tissue, submucosal tissue, dura mater, and the like), polytetrafluoroethylene (ePTFE), polyester or polyurethane. The root component 40 may be fixed in an identical or similar manner as the tissue component 38. The root component 40 is securely attached to the tissue component 38 using, for example, sutures or any other known attachment means (e.g., pins, clips, staples, adhesives, and the like). It will be appreciated that the tissue component 38 may be treated with the aqueous treatment solution prior to the time it is fashioned into the substantially dehydrated bioprosthetic valve 32, after it is fashioned into the substantially dehydrated bioprosthetic valve, or at both stages in the manufacture of the substantially dehydrated bioprosthetic valve.

Figure 6:
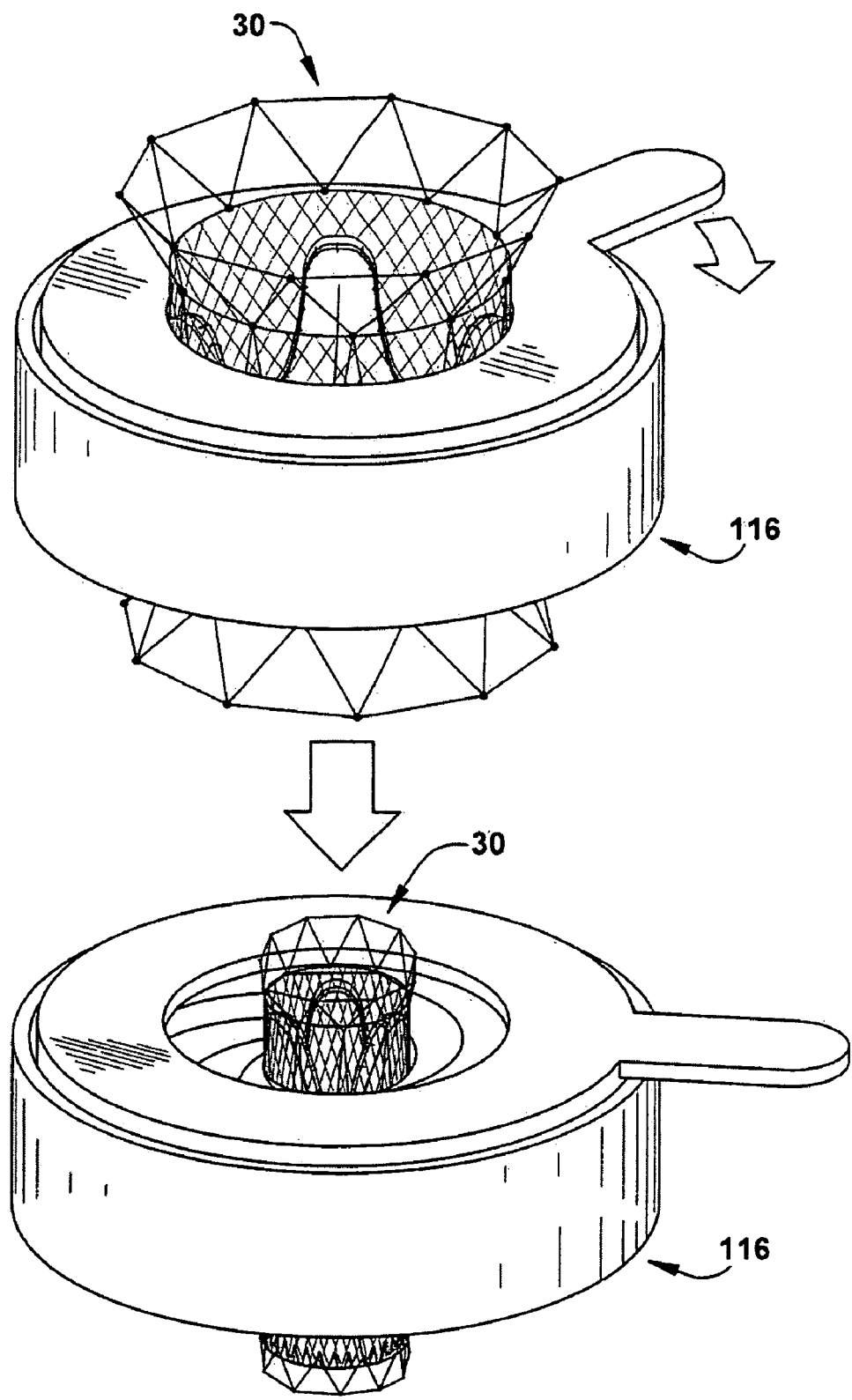
FIG. 6 is a perspective view showing a process for collapsing the expandable support member shown in FIG. 3 into a compressed configuration.

After the tissue component 38 is securely attached to the root component 40, an expandable support member 34 is then provided at 14. As shown in FIG. 3, the expandable support member 34 comprises oppositely disposed first and second ends 42 and 44 and a main body portion 46 extending between the ends. The expandable support member 34 has a known stent configuration that allows it to be expanded and compressed (FIG. 6). The flexible and expandable properties of the expandable support member 34 facilitate percutaneous delivery of the valve 30.

The expandable support member 34 may be made from any suitable medical grade metal or plastic, including shape memory materials such as Nitinol, stainless steel, and/or titanium. Additionally, at least a portion of the expandable support member 34 may be made from a bioabsorbable material including, for example, magnesium alloy, dendrimers, biopolymers such as thermoplastic starch, polyalctides, cellulose, and aliphatic aromatic copolyesters.

The expandable support member 34 is generally annular in shape and may be comprised of a continuous series of W-shaped segments 48 collectively forming a mesh-like configuration. It is contemplated, however, that other geometries may be used. As shown in FIG. 3, the W-shaped segments 48 comprising the first and second ends 42 and 44 extend radially from the main body portion 46 of the expandable support member 34. As described in more detail below, the radial configuration of the first and second ends 42 and 44 facilitates implantation of the valve 30. It should be appreciated that the substantially dehydrated bioprosthetic valve 32 may be formed (i.e., treated) after attachment to the expandable support member 34.

It should also be appreciated that the valve 30 may include other bioprosthetic valves known in the art. For example, the valve 30 may be constructed in an identical or similar fashion as the bioprosthetic valves illustrated in FIGS. 5A and 5B and disclosed in U.S. Patent Pub. Nos. 2006/0195183 A1 and 2006/0259135 A1, the entireties of which are hereby incorporated by reference.

Figure 5A:
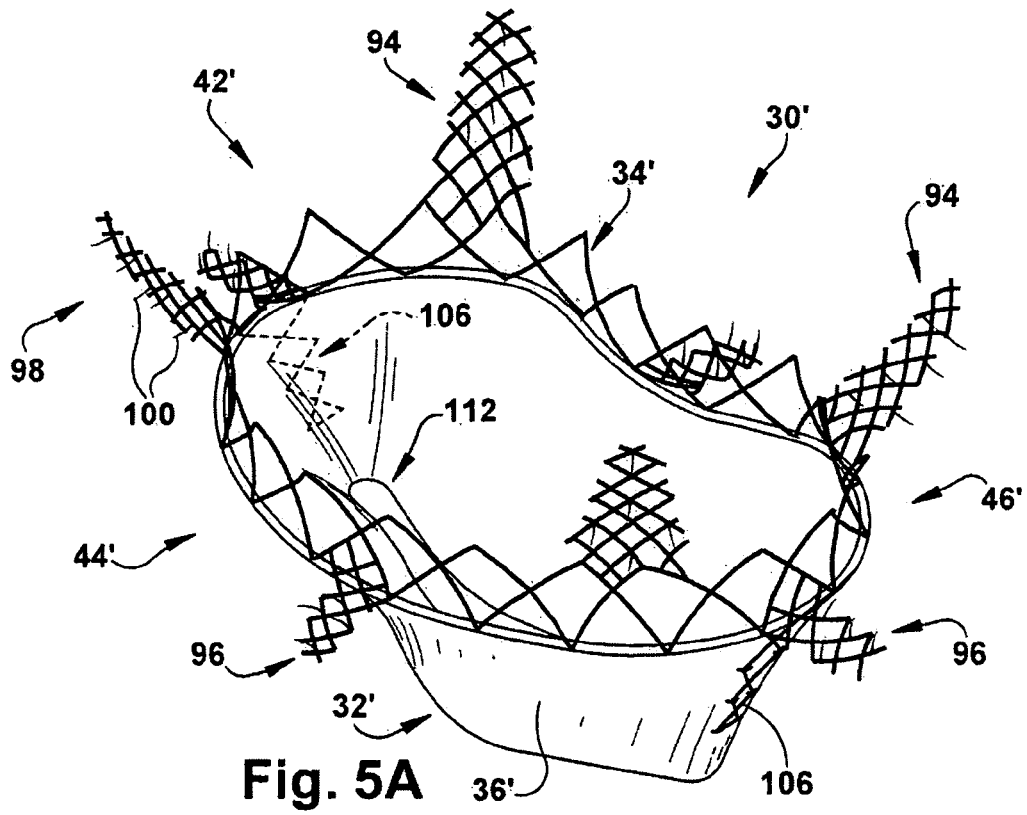
FIG. 5A is a perspective view showing an alternative embodiment of the valve in FIG. 3.
Figure 5B:
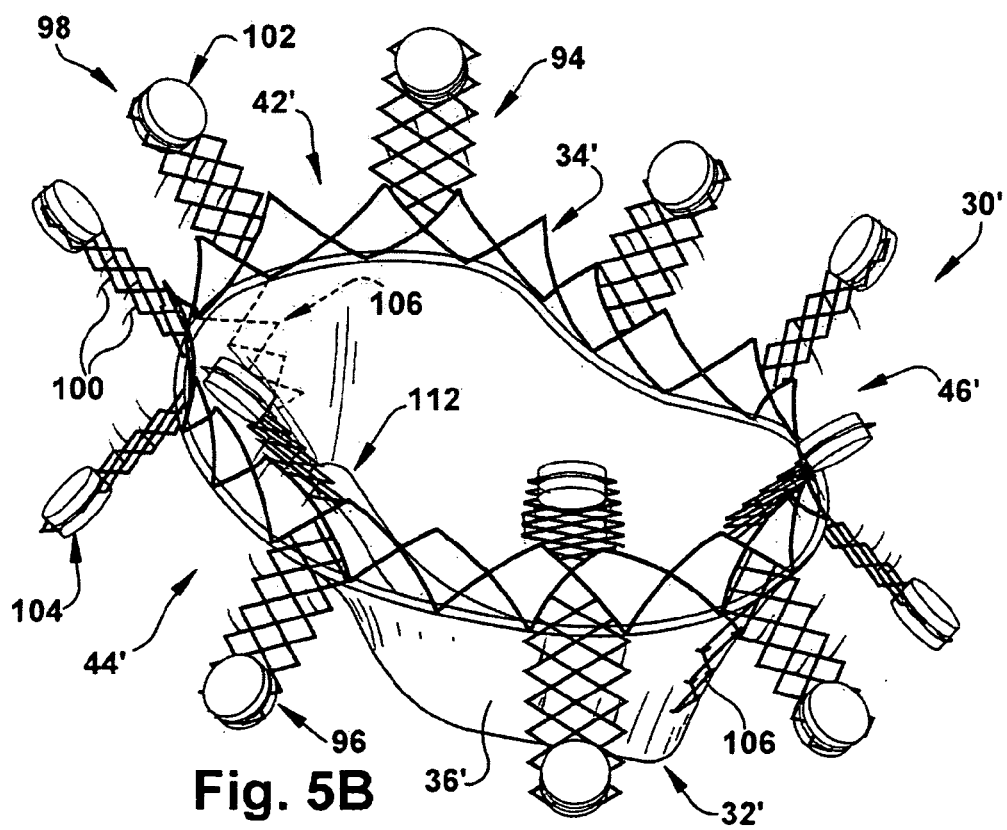
FIG. 5B is a perspective view showing another alternative embodiment of the valve in FIG. 5A.

As illustrated in FIGS. 5A and 5B, a valve 30' can comprise an expandable support member 34' having oppositely disposed first and second ends 42' and 44' and a main body portion 46' extending between the ends. The first and second ends 42' and 44' of the expandable support member 34' can respectively include a plurality of upper and lower wing members 94 and 96 that extend from the main body portion 46' and are spaced circumferentially apart about the main body portion. Each of the upper and lower wing members 94 and 96 can include at least one attachment mechanism 98. As shown in FIG. 5A, for example, the at least one attachment mechanism 98 can comprise a barb 100 or hook capable of embedding into cardiovascular tissue.

Alternatively, each of the upper and lower wing members 94 and 96 can respectively include first and second magnetic components 102 and 104 as shown in FIG. 5B. The first and second magnetic components 102 and 104 may be magnetically attracted to one another so that, when the valve 30' is placed in the annulus 90 (FIG. 12) of a mitral valve 70, for example, the upper and lower wing members 94 and 96 (FIGS. 5A and 5B) are pulled toward one another to secure the valve in the mitral annulus. The second end 44' of the expandable support member 34' may also include at least two strut members 106 that are spaced apart from each other.

A tissue component 38', such as a substantially dehydrated bioprosthetic valve 32', may be secured within the main body portion 46' of the expandable support member 34' as shown in FIGS. 5A and 5B. For example, the substantially dehydrated bioprosthetic valve 32' can comprise a valve having at least two valve leaflets that are coaptable to permit unidirectional blood flow. It should be appreciated that the tissue component 38' may alternatively have a tri-leaflet configuration (not shown). Each of the at least two valve leaflets may be joined together at least two commissural sections 112 that are spaced apart from each other. Each of the at least two commissural sections 112 may be attached to a respective one of the strut members 106 to prevent prolapse of the valve leaflets.

Referring again to FIG. 3, the expandable support member 34 may further include a layer 80 of biocompatible material covering at least a portion of the expandable support member 34. The layer 80 of biocompatible material may be synthetic, such as polyester (e.g., Dacron®) (Invista, Wichita, Kans.), woven velour, polyurethane, PTFE, ePTFE, Gore-Tex® (W.L. Gore & Associates, Flagstaff, Ariz.), or heparin-coated fabric. Alternatively, the layer 80 may be a biological material such as bovine, equine, and/or porcine pericardium, peritoneal tissue, pleura, submucosal tissue, dura mater, an allograft, a homograft, a patient graft, or a cell-seeded tissue.

The layer 80 can cover either the inside surface of the expandable support member 34, the outside surface of the expandable support member, or can be wrapped around both the inside and outside surfaces. The layer 80 may be attached around the entire circumference of the expandable support member 34 or, alternatively, may be attached in pieces or interrupted sections to allow the expandable support member to more easily expand and contract. As shown in FIG. 3, for example, only the main body portion 46 of the expandable support member 34 may be covered with the layer 80 of biocompatible material. The entire expandable support member 34 may be entirely covered with the layer 80 of biocompatible material or, alternatively, not covered at all.

To facilitate positioning of the valve 30 in the cardiovascular system of a subject, the expandable support member 34 may include at least one radiographically opaque marking (not shown). The radiographically opaque marking may be located at any other portion of the expandable support member 34. The radiographically opaque marking can be any one or combination of materials or devices with significant opacity. Examples of such radiographically opaque markings include, but are not limited to, a steel mandrel sufficiently thick to be visible on fluoroscopy, a tantalumlpolyurethane tip, a gold-plated tip, bands of platinum, stainless steel or gold, soldered spots of gold, and polymeric materials with a radiographically opaque filler such as barium sulfate.

The expandable support member 34 may also include at least one therapeutic agent for eluting into the cardiovascular tissue and/or blood stream. The therapeutic agent may be capable of preventing a variety of pathological conditions including, but not limited to, hypertension, hypotension, arrhythmias, thrombosis, stenosis and inflammation. Accordingly, the therapeutic agent may include at least one of an anti-arrhythmic agent, an anti-hypertensive, an anti-hypotensive agent, an anticoagulant, an antioxidant, a fibrinolytic, a steroid, an anti-apoptotic agent, an anti-mineralization agent, an anti-calcification agent, and/or an anti-inflammatory agent.

Optionally or additionally, the therapeutic agent may be capable of treating or preventing other diseases or disease processes such as microbial infections and heart failure. In these instances, the therapeutic agent may include an inotropic agent, a chronotropic agent, an anti-microbial agent, and/or a biological agent such as a cell, peptide, or nucleic acid. The therapeutic agent can be linked to a surface of the expandable support member 34, embedded and released from within polymer materials, such as a polymer matrix, or surrounded by and released through a carrier.

After the substantially dehydrated bioprosthetic valve 32 is securely attached to the expandable support member 34, the expandable support member is crimped into a compressed configuration at 18 (FIG. 6). The expandable support member 34 may be crimped using tactile means, for example, or by any other method, including various mechanical-based devices, such as the device 116 illustrated in FIG. 6, known in the art. Crimping the expandable support member 34 into a compressed configuration facilitates percutaneous delivery of the valve 30 at 132. The crimped valve 30 is then stored in an environment (not shown) essentially free of liquid for later processing or implantation. It will be appreciated that the valve 30 may also be stored in the expanded configuration.

An environment, container (not shown), or package (not shown) that is "essentially free of liquid" as described herein refers to a non-fluid environment in which the presence of water or other liquids is limited to the content of such liquids in the ambient air (as more precisely defined by the relative humidity), and the content of liquid contained within the substantially dehydrated bioprosthetic valve 32 disposed within a container or package. For example, the valve 30 may be placed into the chamber of a microorganism-resistant container. After the valve 30 is placed in the chamber at 132, the chamber is sealed and sterilized at 134 by, for example, exposure to ionizing radiation or a sterilizing gas (e.g., ethylene oxide). Alternatively, the valve 30 may be placed in a delivery catheter 86 and the delivery catheter then stored in a container essentially free of liquid.

At 20, the valve 30 is placed at a desired location within the cardiovascular system of a subject. As illustrated in FIGS. 7-13, for example, the valve 30 may be placed within the cardiovascular system of a subject to replace a diseased mitral valve 70. It should be appreciated, however, that the valve 30 may be implanted at any desired location within the cardiovascular system of subject, including, for example, in place of a tricuspid valve 68, an aortic valve, a pulmonary valve, a pulmonary artery (not shown) or vein 66, a venous valve, an inferior vena cava 64, a superior vena cava 62, or any other peripheral artery or venous valve.

Prior to placement of the valve 30 at the desired location, the dimensions of the diseased mitral valve 70 are determined using known imaging techniques including, for example, magnetic resonance imaging (MRI), fluoroscopy, computed tomography (CT), angiography, ultrasound, and combinations thereof. After determining the dimensions of the diseased mitral valve 70, an appropriately-sized valve 30 having dimensions that correspond to the dimensions of the diseased mitral valve is selected.

Figure 7:
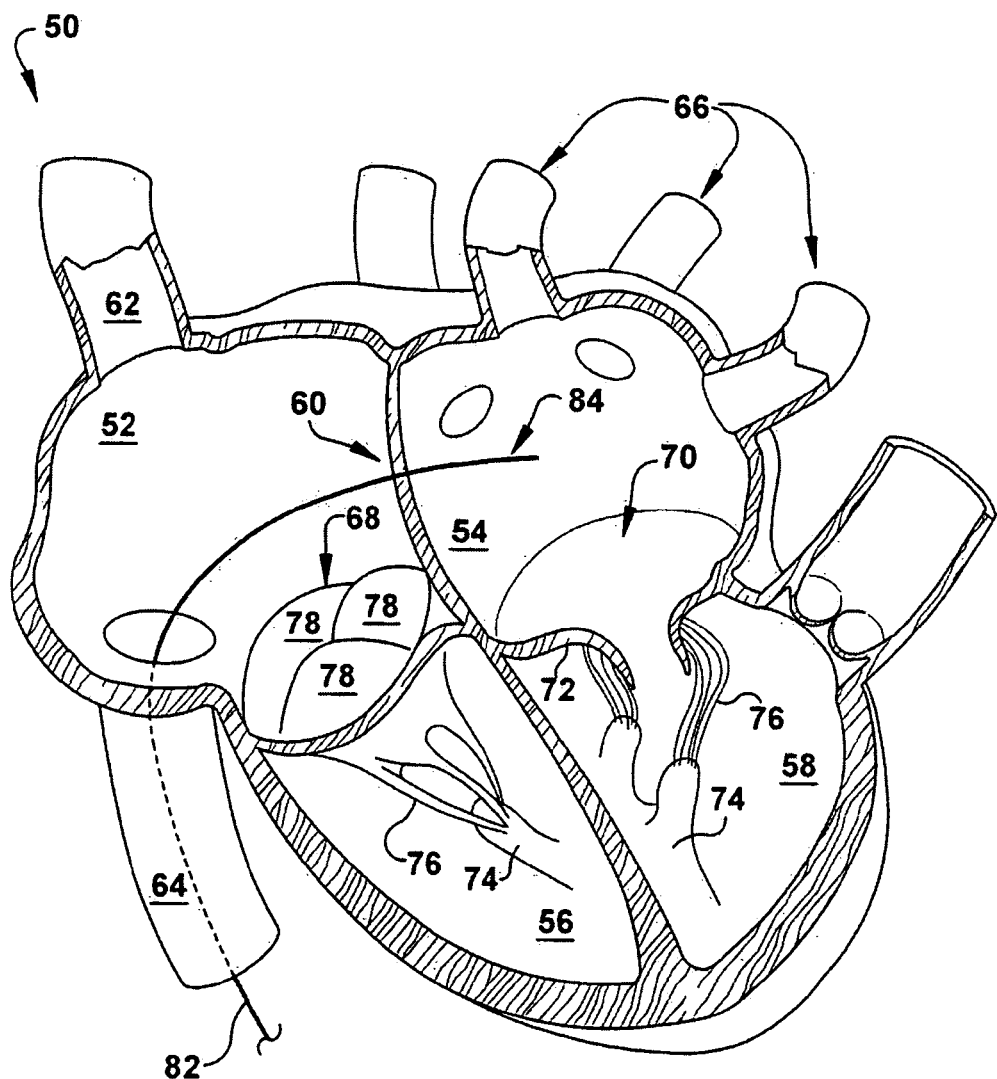
FIG. 7 is a cross-sectional view showing a guidewire extending trans-septally through a human heart.
Figure 8:
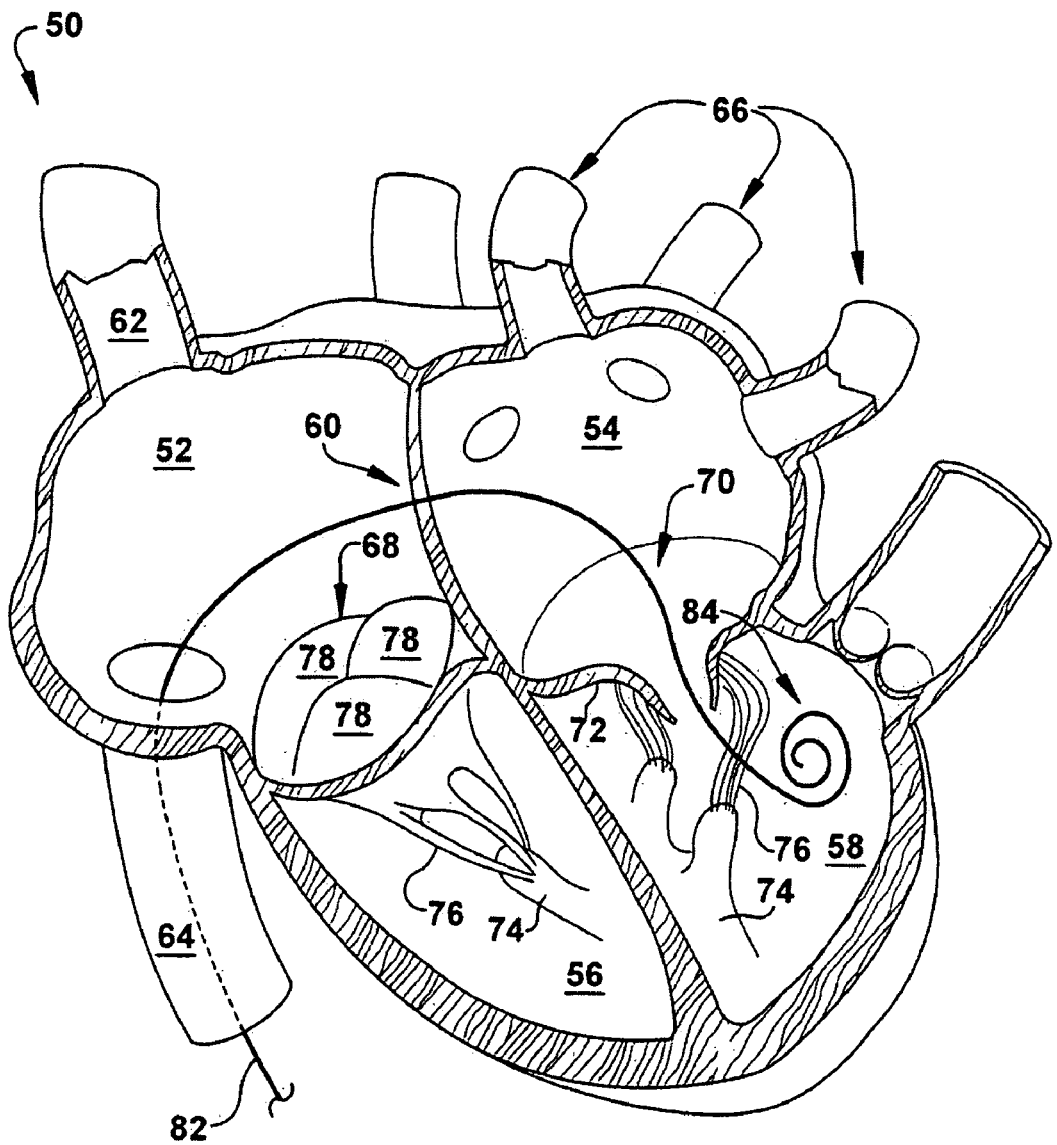
FIG. 8 is a cross-sectional view showing the guidewire extending through the mitral valve into the left ventricle.

Next, a guidewire 82 is inserted into the vasculature of the subject via a femoral vein (not shown) or jugular vein (not shown) and, under image guidance (e.g., fluoroscopy, ultrasound, MRI, CT, or combinations thereof), respectively steered through the vasculature of the subject into the inferior vena cava 64 or superior vena cava 62. The guidewire 82 is then passed across the right atrium 52 so that the distal end 84 of the guidewire pierces the interatrial septum 60 as shown in FIG. 7. The guidewire 82 is extended across the left atrium 54 and then downward through the diseased mitral valve 70 so that the distal end 84 of the guidewire is securely positioned in the left ventricle 58 (FIG. 8).

Figure 9:
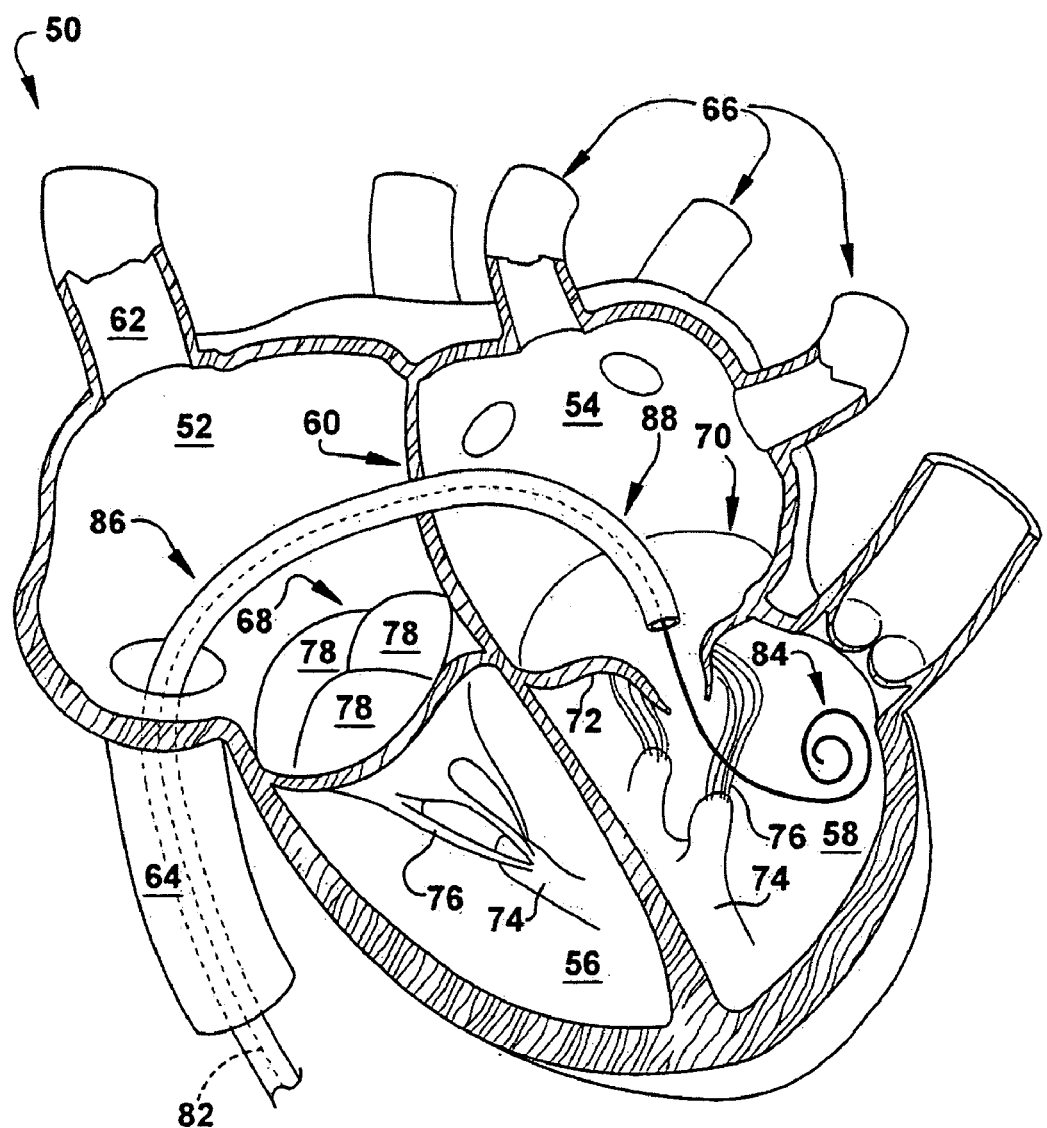
FIG. 9 is a cross-sectional view showing a delivery catheter advanced over the guidewire.
Figures 10A, 10B:
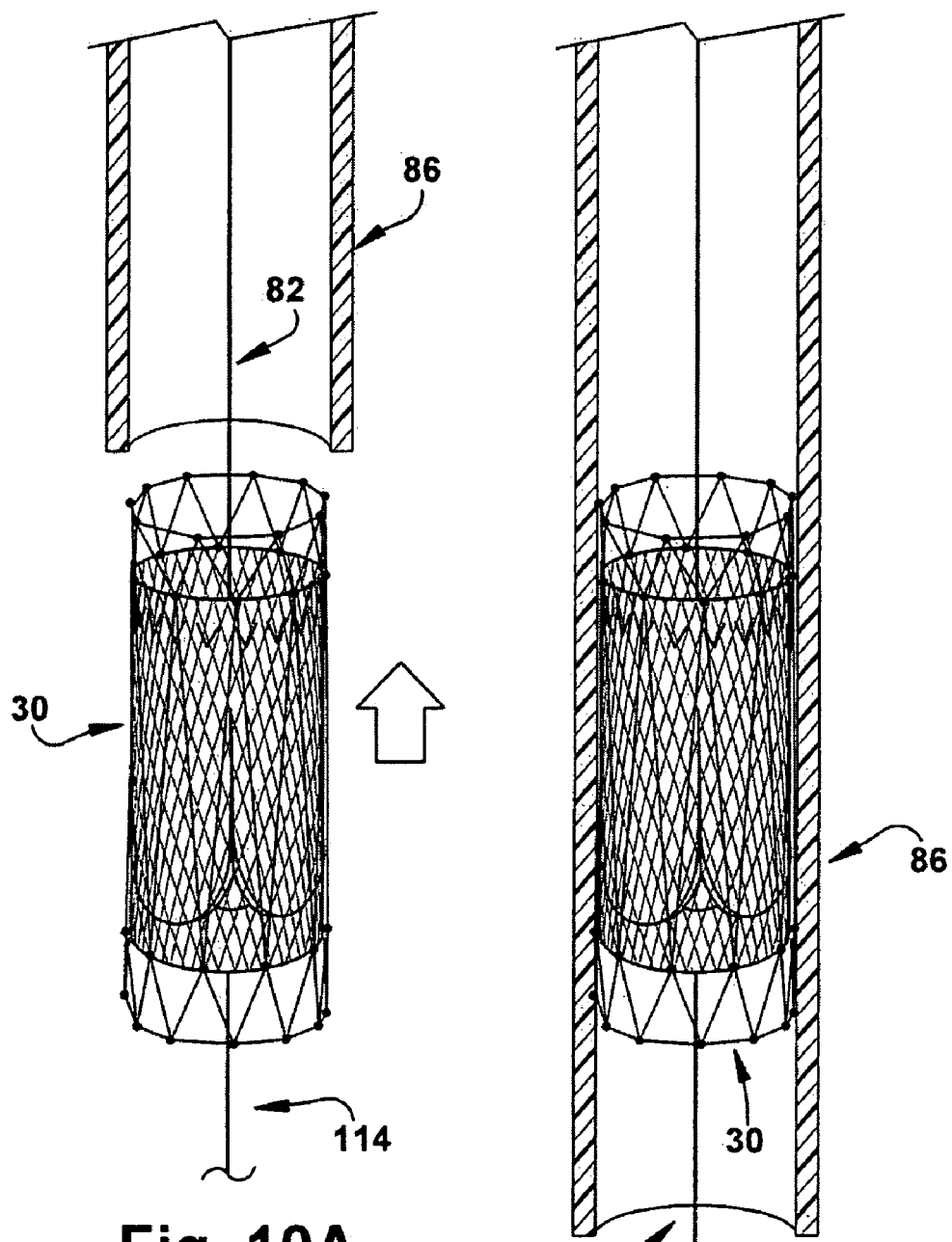
FIG. 10A is a perspective view showing the valve of FIG. 6 attached to the guidewire.
FIG. 10B is a perspective view showing the valve of FIG. 10A loaded into the delivery catheter.
Figure 11:
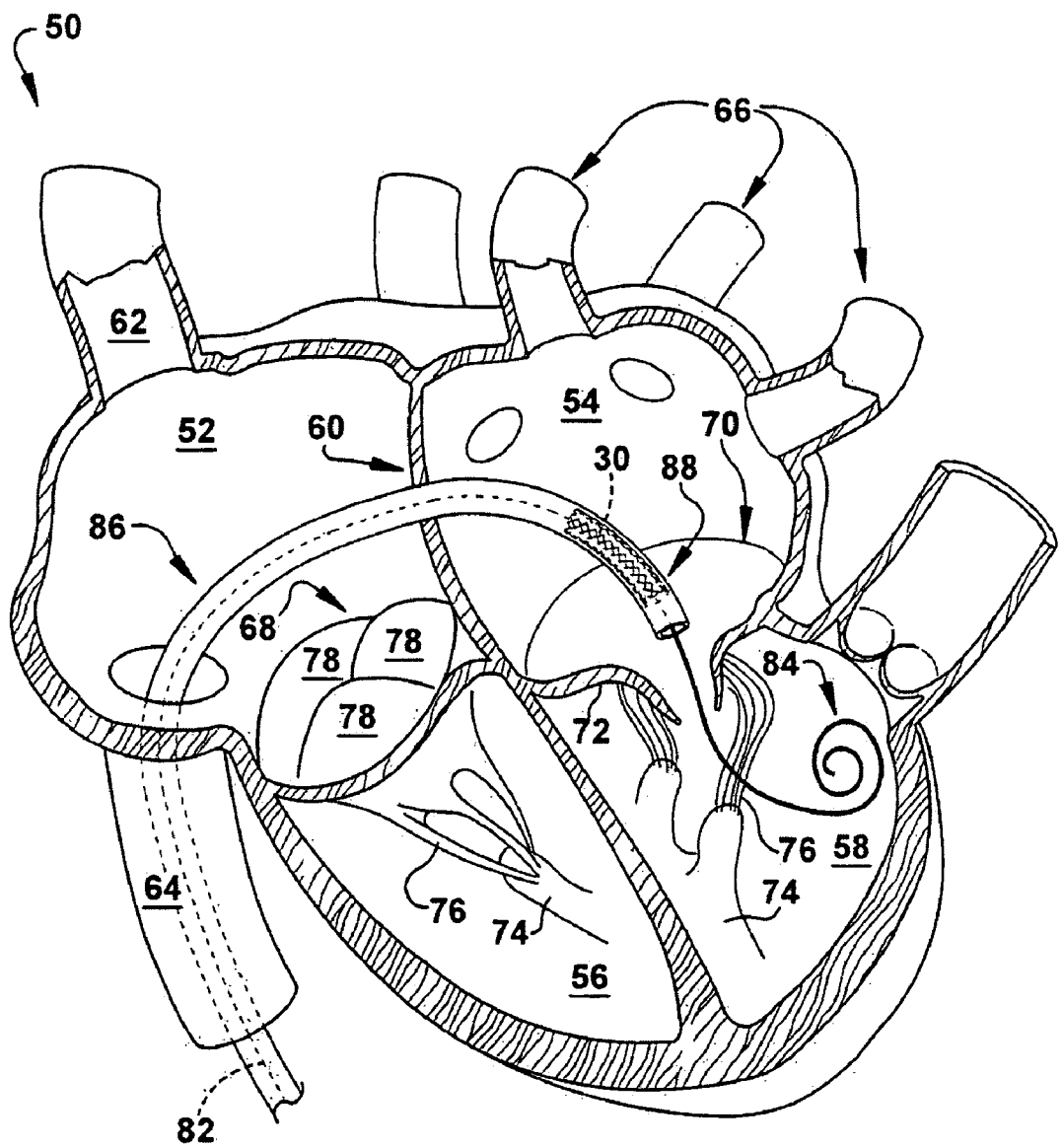
FIG. 11 is a cross-sectional view showing the valve of FIG. 10B positioned at a distal end of the delivery catheter.

After the guidewire 82 is appropriately positioned in the heart 50, a delivery catheter 86 is passed over the guidewire as shown in FIG. 9. The delivery catheter 86 may be comprised of a flexible, resiliently yieldable material such as silicone, PTFE, ePTFE, plastic polymer, or the like. After the delivery catheter 86 is positioned as shown in FIG. 9, the appropriately-sized valve 30 is removed from the sterile container, attached to the proximal end 114 of the guidewire 82 (FIG. 10A), and loaded into the delivery catheter (FIG. 10B). If needed, the valve 30 may be rinsed with a sterile solution or liquid, such as sterile saline or water, just prior to loading the valve into the delivery catheter 86. A positioning wire (not shown) or other similar device useful for advancing the valve 30 over the guidewire 82 is then attached to the valve. An axial force is then applied to the positioning wire so that the valve 30 is passed over the guidewire 82 and positioned at the distal end 88 of the delivery catheter 86 (FIG. 11).

Figure 12:
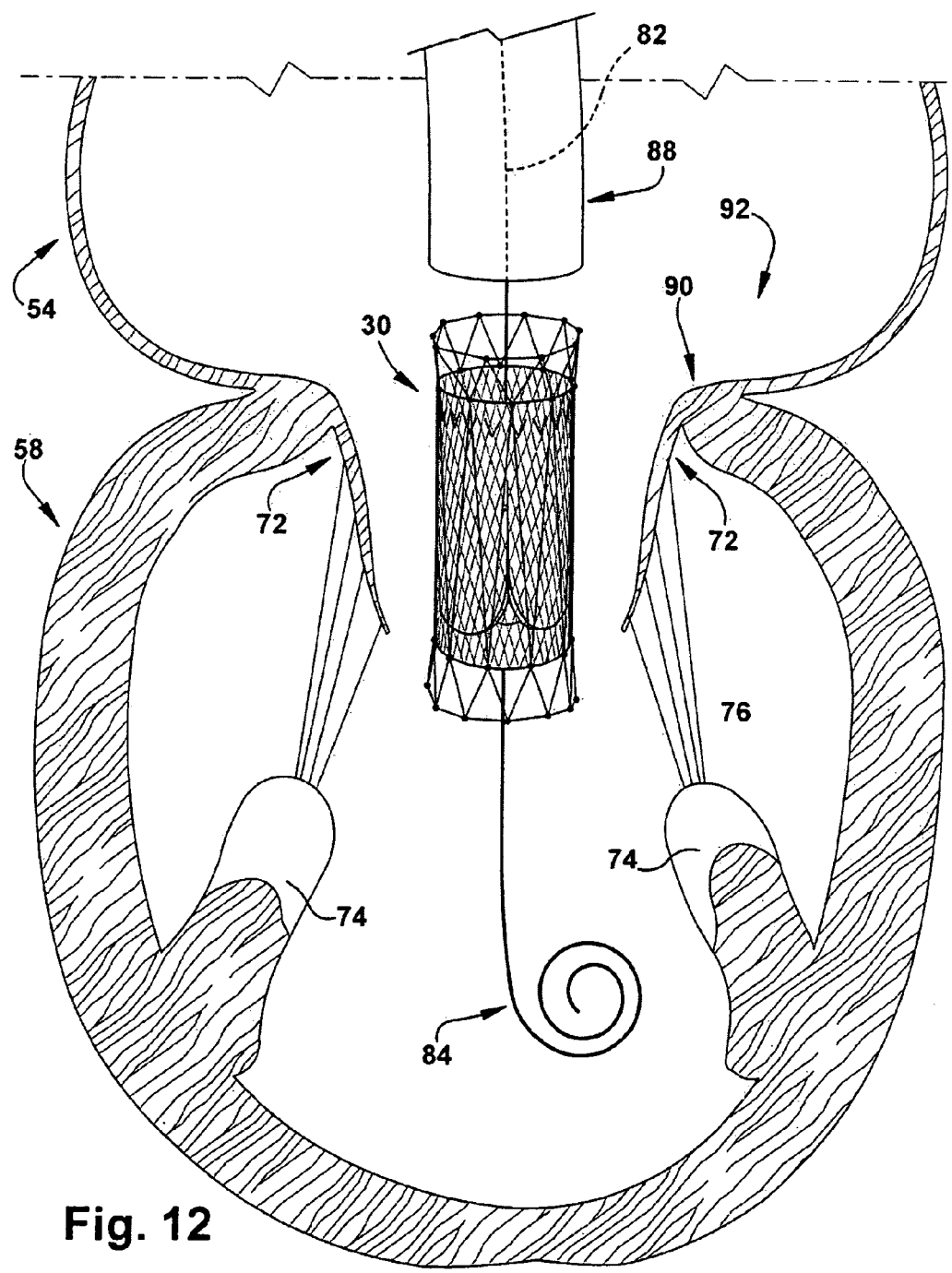
FIG. 12 is a cross-sectional view of a magnified mitral valve showing the valve of FIG. 6 being delivered to the mitral valve.

Upon reaching the distal end 88 of the delivery catheter 86, the valve 30 is progressively freed from the delivery catheter and positioned in the mitral annulus 90 as shown in FIG. 12.

As the valve 30 is progressively freed from the delivery catheter 86, the position of the valve in the left atrium 54 can be monitored, controlled, and/or quality assured by imaging systems of various kinds. For example, X-ray machines, fluoroscopic machines, ultrasound, CT, MRI, positron emission tomography (PET), and other imaging devices may be used.

Figure 13:
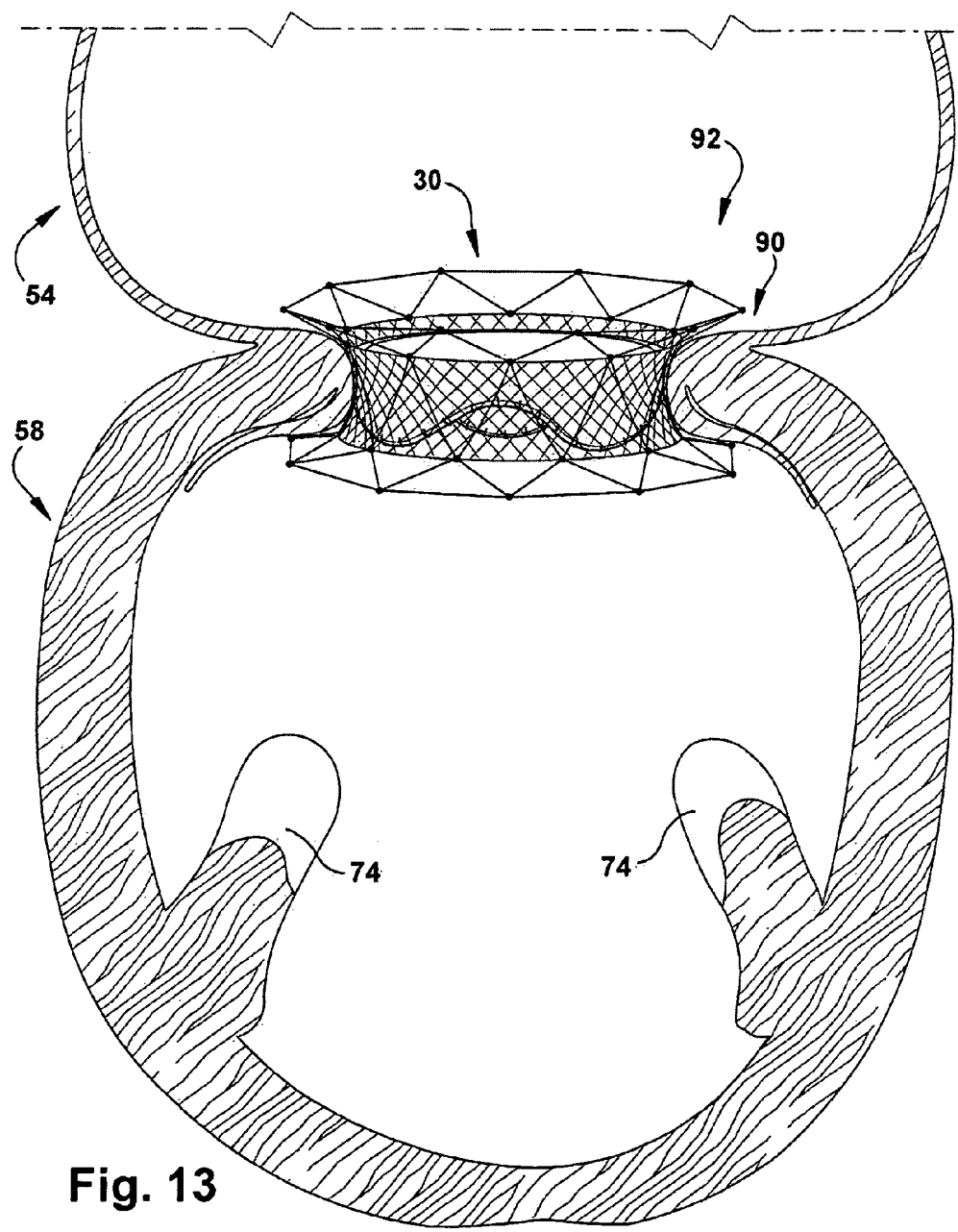
FIG. 13 is a cross-sectional view of a magnified mitral valve showing the valve of FIG. 3 securely positioned in place of the mitral valve.

As shown in FIG. 13, the expandable support member 34 obtains an expanded configuration at 22 as the expandable support member is progressively freed from the delivery catheter 86. In the expanded configuration, the first end 42 of the expandable support member 34 engages the superior aspect 92 of the mitral valve annulus 90, and the second end 44 displaces the mitral leaflets 72 so that the leaflets are pinned back against the annulus of the mitral valve. With the valve 30 securely positioned in the mitral annulus 90, blood flows through the expandable support member 34 and contacts the substantially dehydrated bioprosthetic valve 32. As the blood contacts the substantially dehydrated bioprosthetic valve 32, the interstices of the substantially dehydrated bioprosthetic valve are re-hydrated, causing the substantially dehydrated bioprosthetic valve to obtain its original (or substantially original) properties and assume normal (or substantially normal) blood flow performance (FIGS. 21-25). Because the valve 30 has been prepared and conditioned prior to delivery, the time needed to prepare the valve for delivery in the operating room is significantly reduced. Additionally, comparable devices prepared in the operating room do not provide such a consistent quality of manufacture as does the valve 30 of the present invention.

Figure 14:
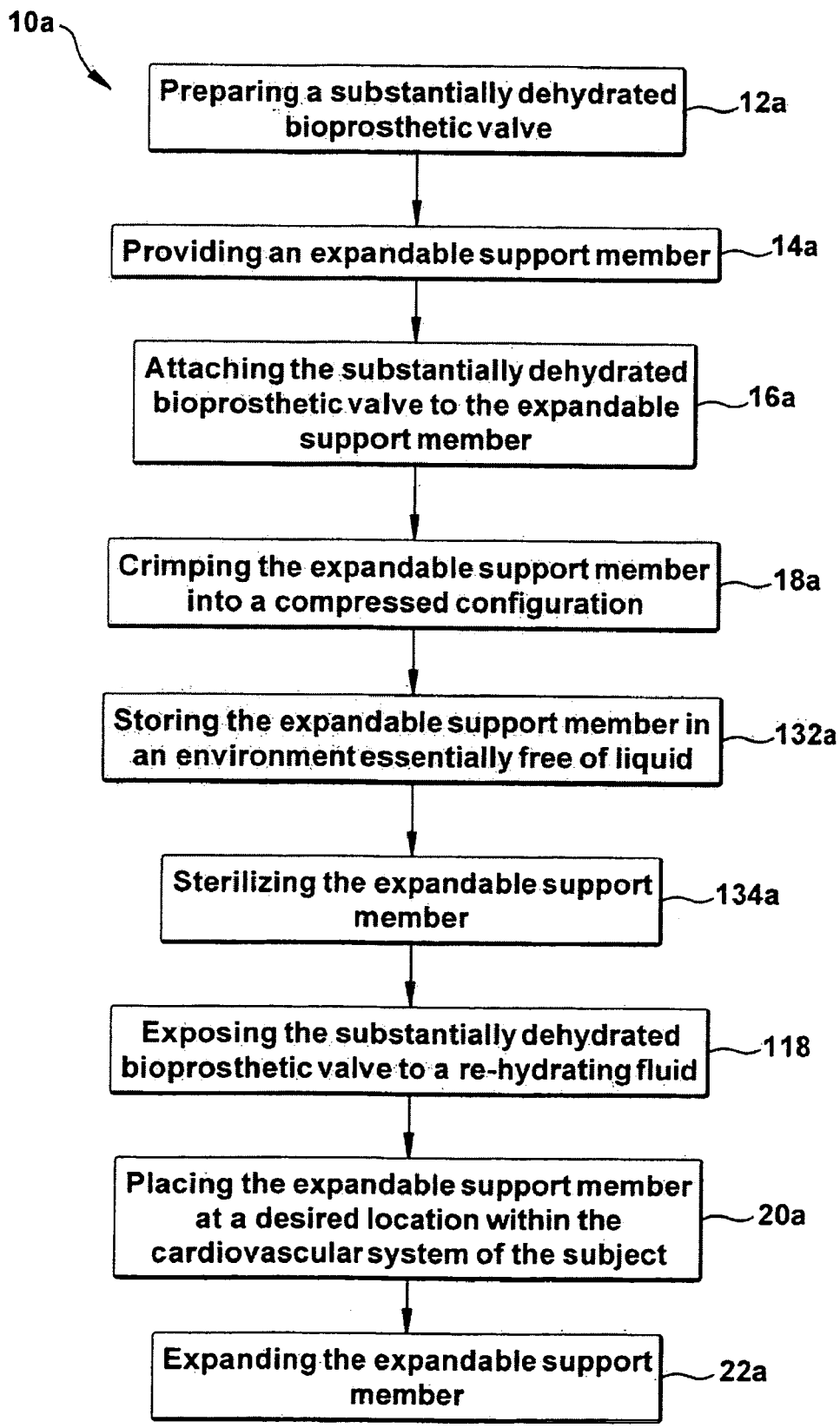
FIG. 14 is a flow diagram illustrating an alternative embodiment of the present invention.

Another embodiment of the present invention is illustrated in FIG. 14. In FIG. 14, a method $10_a$ is provided for implanting a valve 30' having at least one valve leaflet 36' within the cardiovascular system of a subject. The method $10_a$ is identical to the method 10 illustrated in FIG. 1, except where as described below. According to the method $10_a$, a substantially dehydrated bioprosthetic valve 32' may be prepared at $12_a$ and securely attached at $16_a$ to an expandable support member 34' to form the valve 30' shown in FIG. 5A (as described above). As also described above, the expandable support member 34' may then be crimped into a compressed configuration at $18_a$, stored at $132_a$, and then sterilized at $134_a$.

Figures 15A, 15B:
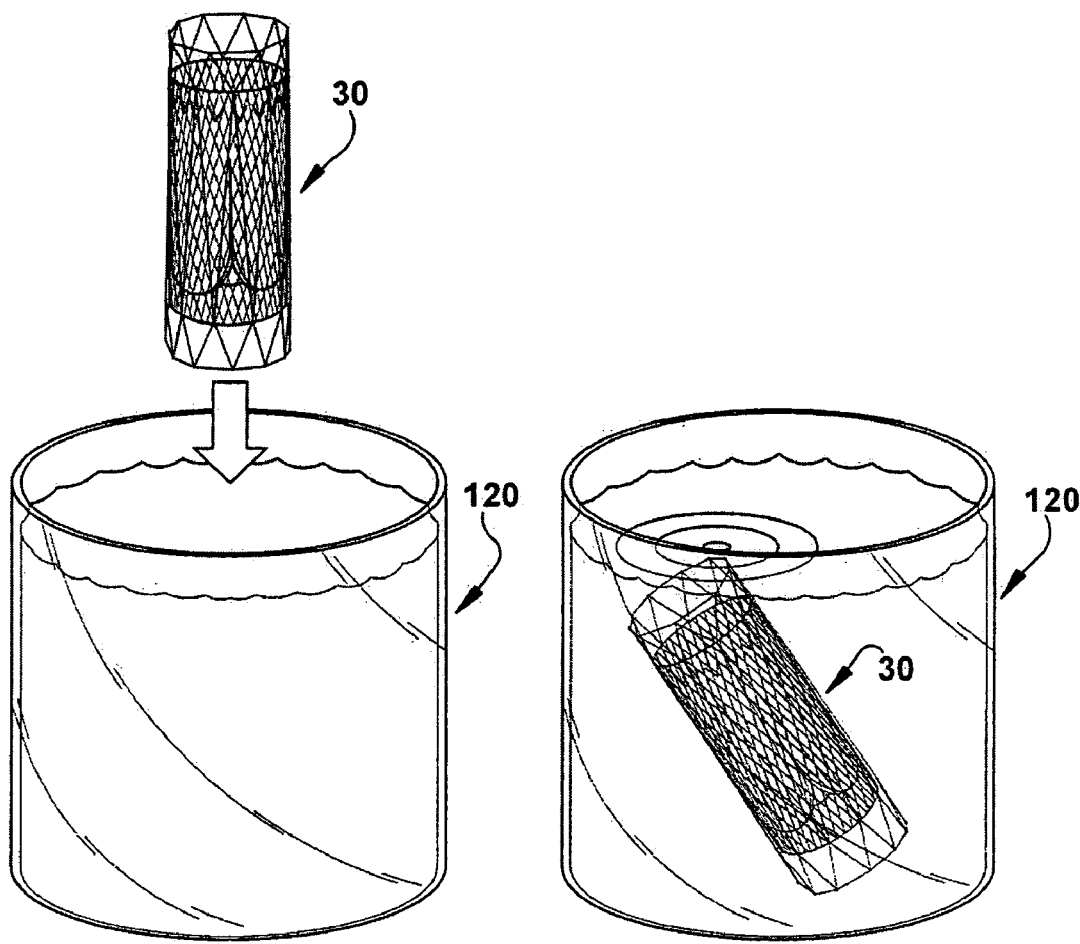
FIG. 15A is a perspective view showing the valve of FIG. 6 being exposed to a re-hydrating fluid.
FIG. 15B is a perspective view showing the valve of FIG. 15A immersed in the re-hydrating fluid.

In the compressed configuration, the substantially dehydrated bioprosthetic valve 32' may be exposed to a re-hydrating fluid at 118 (FIG. 15A). The re-hydrating fluid can comprise saline or sterile water, for example, and may be contained in a suitable container 120. As shown in FIG. 15B, the valve 30' may be immersed in the re-hydrating fluid for a time appropriate so that the substantially dehydrated bioprosthetic valve 32' is re-hydrated and obtains (or substantially obtains) its original properties.

Figure 16:
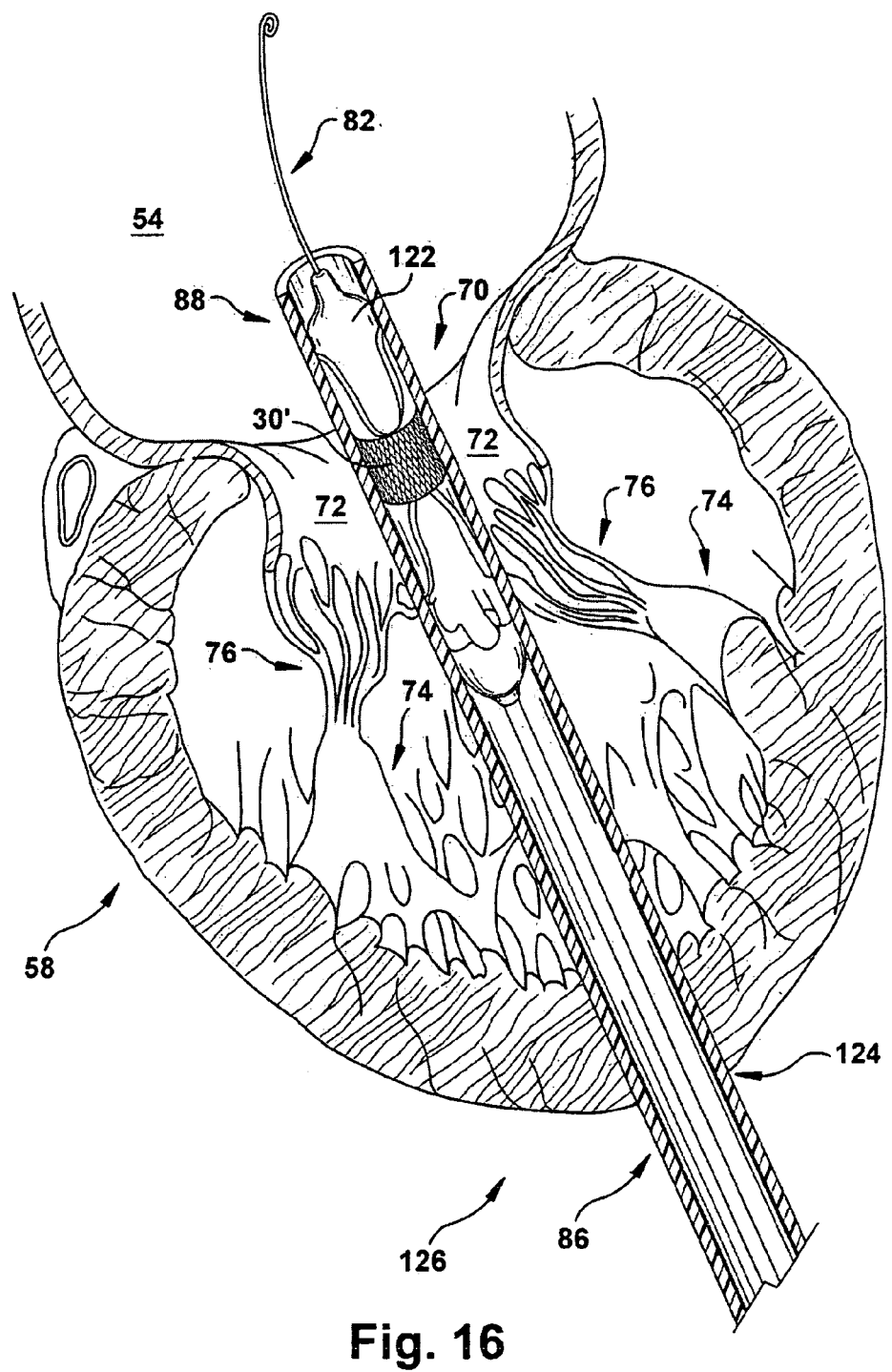
FIG. 16 is a perspective view showing the valve of FIG. 5A contained in a delivery catheter and being delivered to a mitral valve via a port at the left ventricular apex.

As described above, the valve 30' may be loaded into a delivery catheter 86 as shown in FIG. 16. The valve 30' may be operably disposed about an inflatable balloon 122 which may be selectively inflated to expand the valve. It should be appreciated, however, that an inflatable balloon 122 may not be included where the valve 30' is self-expanding. After loading the valve 30' into the delivery catheter 86, access to a desired location within the cardiovascular system of a subject may then be obtained. As shown in FIG. 16, for example, access to a diseased mitral valve 70 of a subject may be obtained via a minimally invasive, open surgical approach whereby a port 124 is created at the left ventricular apex 126. After the port 124 is created, the delivery catheter 86 may be inserted through the port and the distal end 88 of the catheter positioned in the diseased mitral valve 70 as shown in FIG. 16.

Figure 17:
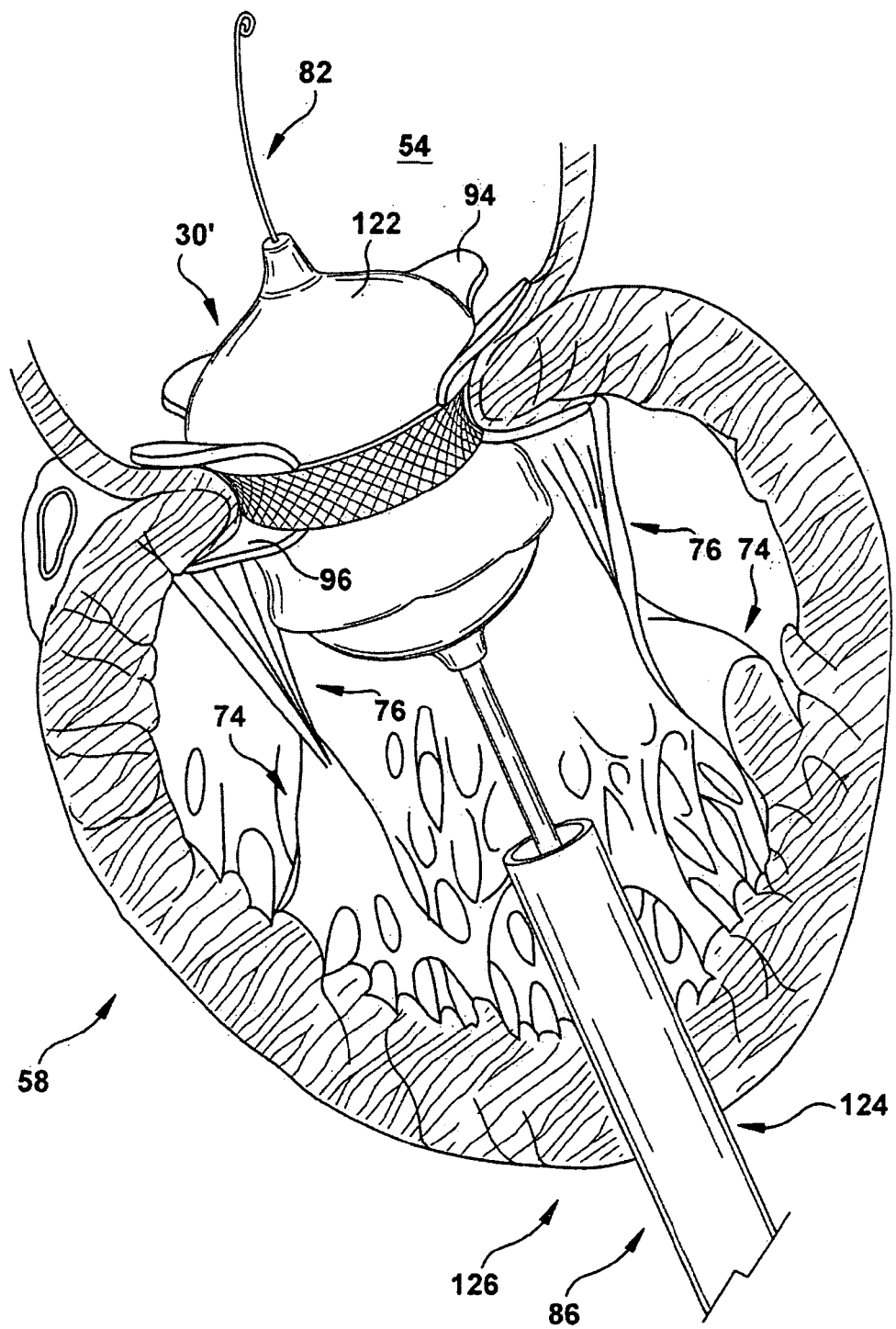
FIG. 17 is a perspective view showing the valve of FIG. 16 in an expanded configuration in place of the mitral valve.

The valve 30' may next be advanced to the distal end 88 of the delivery catheter 86. The delivery catheter 86 may then be progressively withdrawn so that the valve 30' is positioned in the diseased mitral valve 70. Next, the valve 30' may be expanded by inflating the inflatable balloon 122 as shown in FIG. 17. As the valve 30' is expanded, the barbs 100 of the upper and lower wing members 94 and 96 respectively engage the superior and inferior aspects 92 and 128 of the mitral valve annulus 90. In doing so, the lower wing members 96 pin the mitral leaflets 72 against the annular wall and secure the valve 30' in place of the diseased mitral valve 70.

Figure 18:
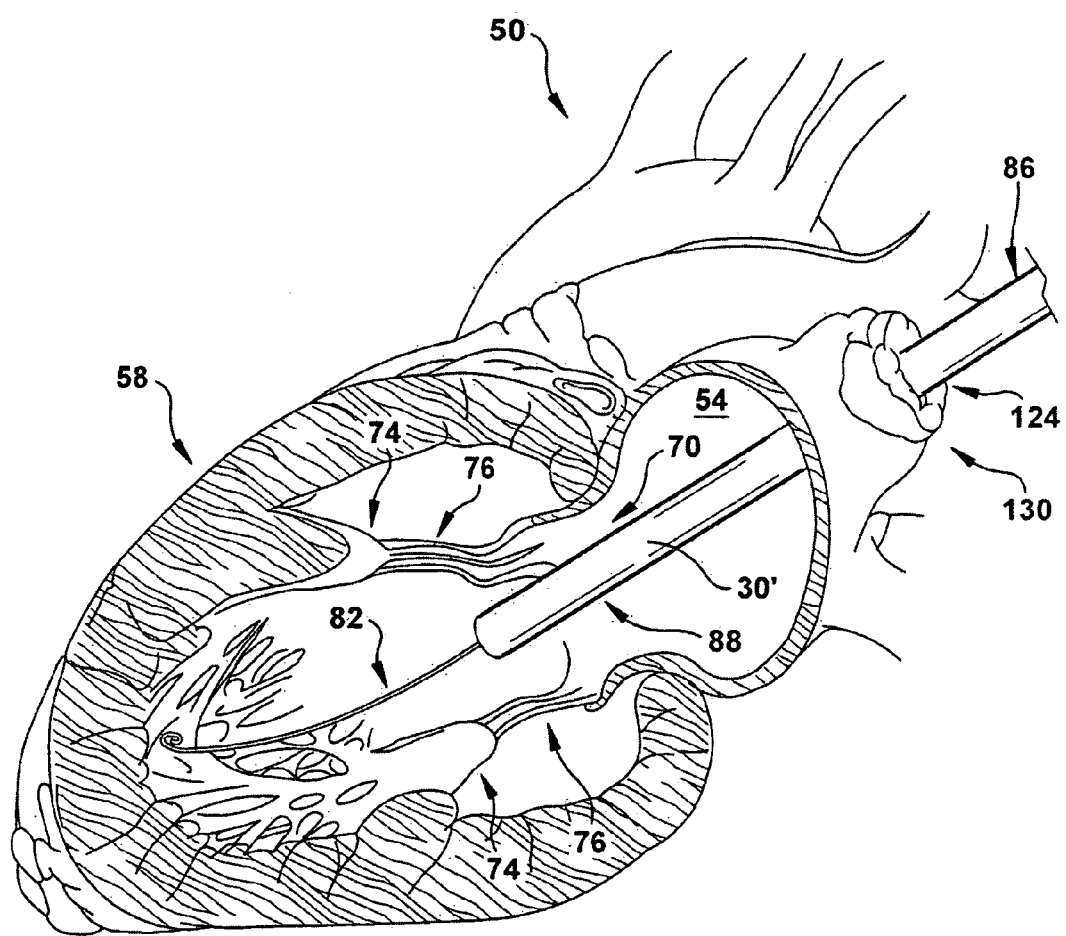
FIG. 18 is a perspective view showing the valve of FIG. 5A contained in a delivery catheter and being delivered to a mitral valve via a port at the left atrial appendage.
Figure 19:
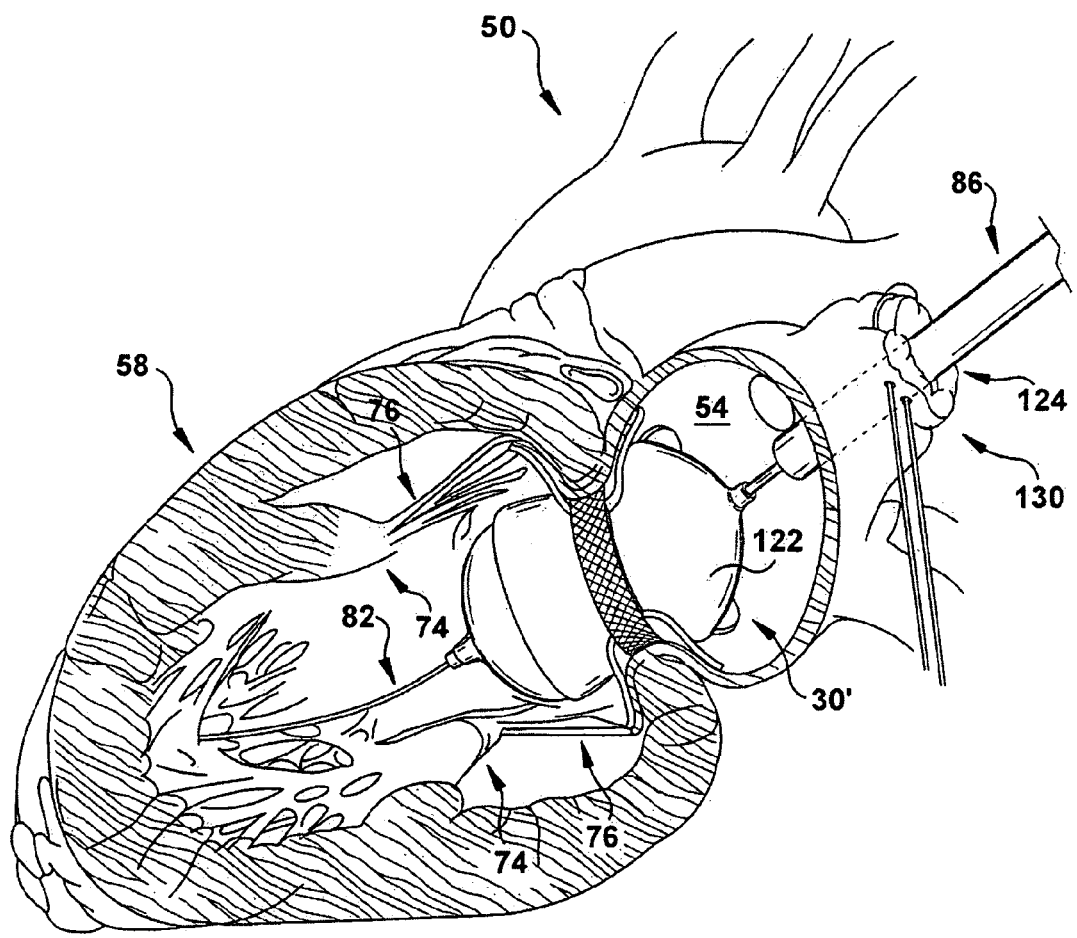
FIG. 19 is a perspective view showing the valve of FIG. 18 in an expanded configuration in place of the mitral valve.

As illustrated in FIGS. 18 and 19, percutaneous access to a desired location within the cardiovascular system of a subject may be obtained via a left atrial appendage 130. Using an open surgical approach, for example, a port 124 or puncture may be made at the left atrial appendage 130 so that a guidewire 82 may be inserted into the port and then threaded through the left atrium 54, across the diseased mitral valve 70, and into the left ventricle 58. Next, a delivery catheter 86 may be advanced over the guidewire 82 so that the distal end 88 of the catheter is positioned in the diseased mitral valve 70 (FIG. 18).

Although not illustrated herein, it should be appreciated that access to other desired locations within the cardiovascular system of a subject may also be obtained using known approaches. For example, access to the tricuspid valve 68, may be obtained via right atrial appendage (not shown). Additionally, for replacement of the aortic valve, access may be obtained through the ascending aorta (not shown) or left ventricular apex 126 (FIG. 16). Alternatively, for replacement of the pulmonary valve (not shown in detail), access may be obtained via the pulmonary artery (not shown), the right ventricle 56, and/or right ventricular outflow track.

The valve 30' may be loaded into the delivery catheter 86 as described above. The valve 30' may then be advanced to the distal end 88 of the delivery catheter 86 as shown in FIG. 18, and then progressively withdrawn from the subject. The inflatable balloon 122 may next be inflated to expand the valve 30' (FIG. 19). Expanding the valve 30' allows the barbs 100 of the upper and lower wing members 94 and 96 to respectively engage the superior and inferior aspects 92 and 128 of the diseased mitral valve 70. In doing so, the lower wing members 96 pin the mitral leaflets 72 against the annular wall and secure the valve 30' in place of the diseased mitral valve 70.

Figure 20:
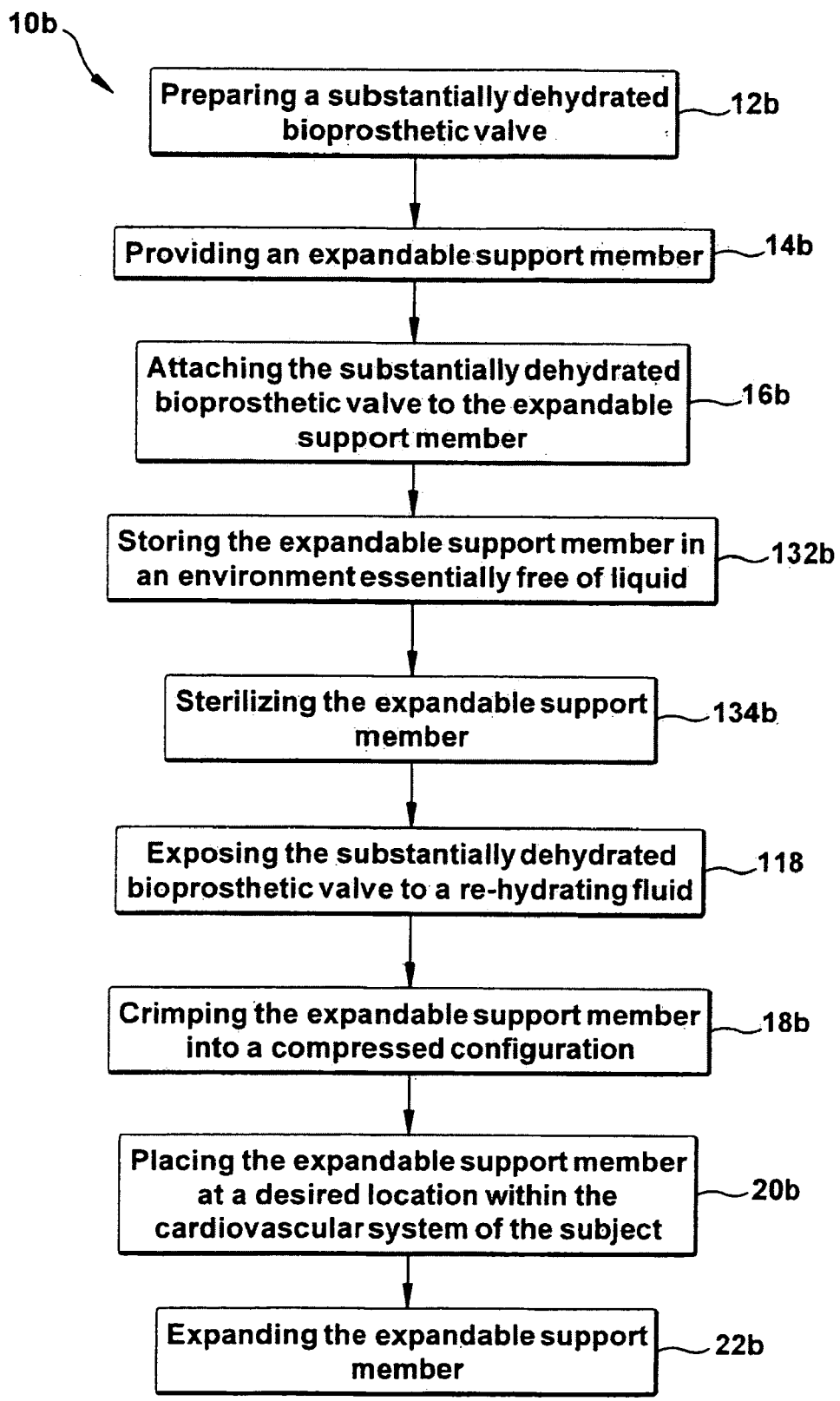
FIG. 20 is a flow diagram illustrating another alternative embodiment of the present invention.
Figure 21:
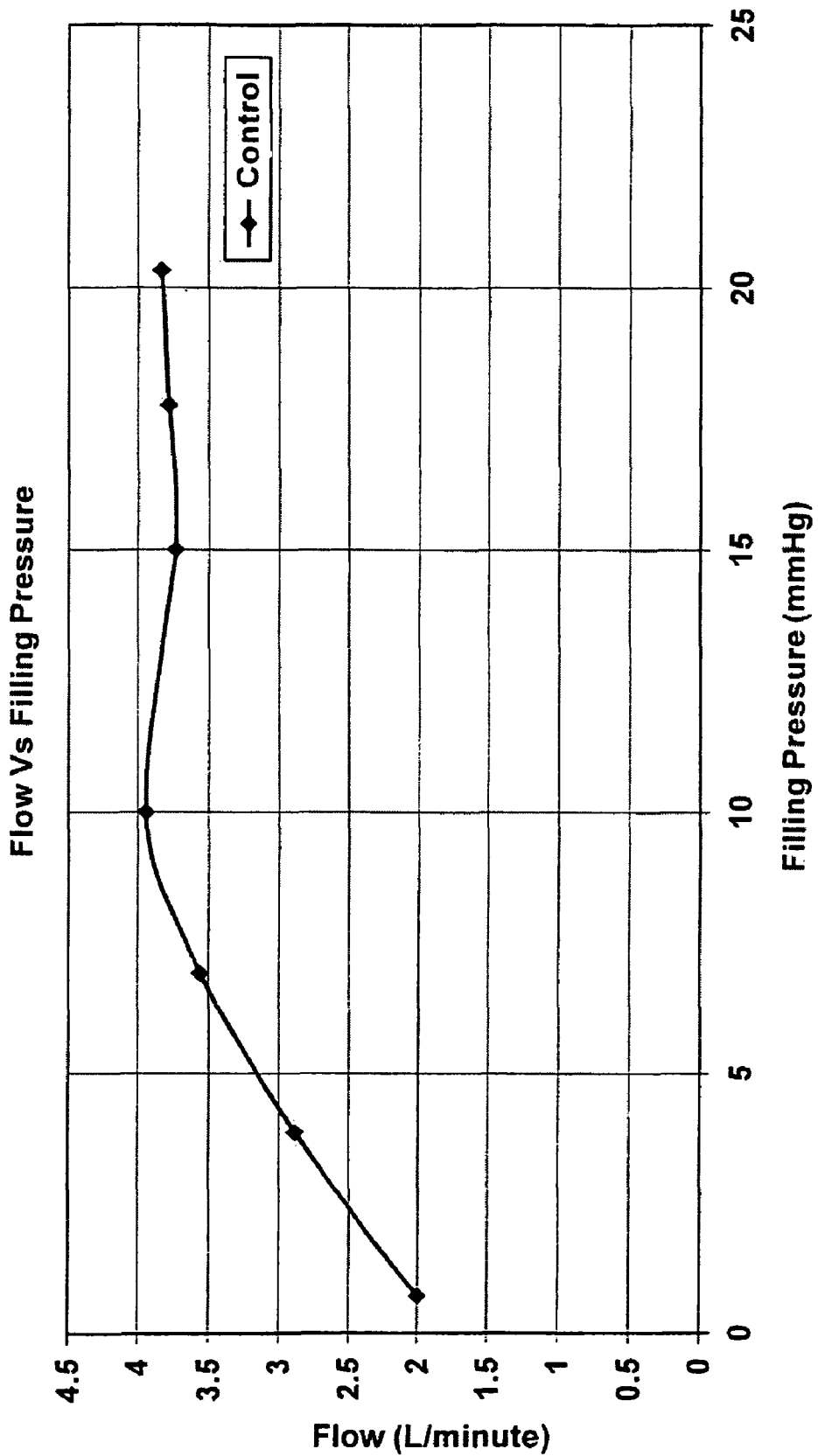
FIG. 21 is a graph depicting the flow performance of a valve comprised of bovine pericardium constructed in accordance with the present invention.
Figure 22:
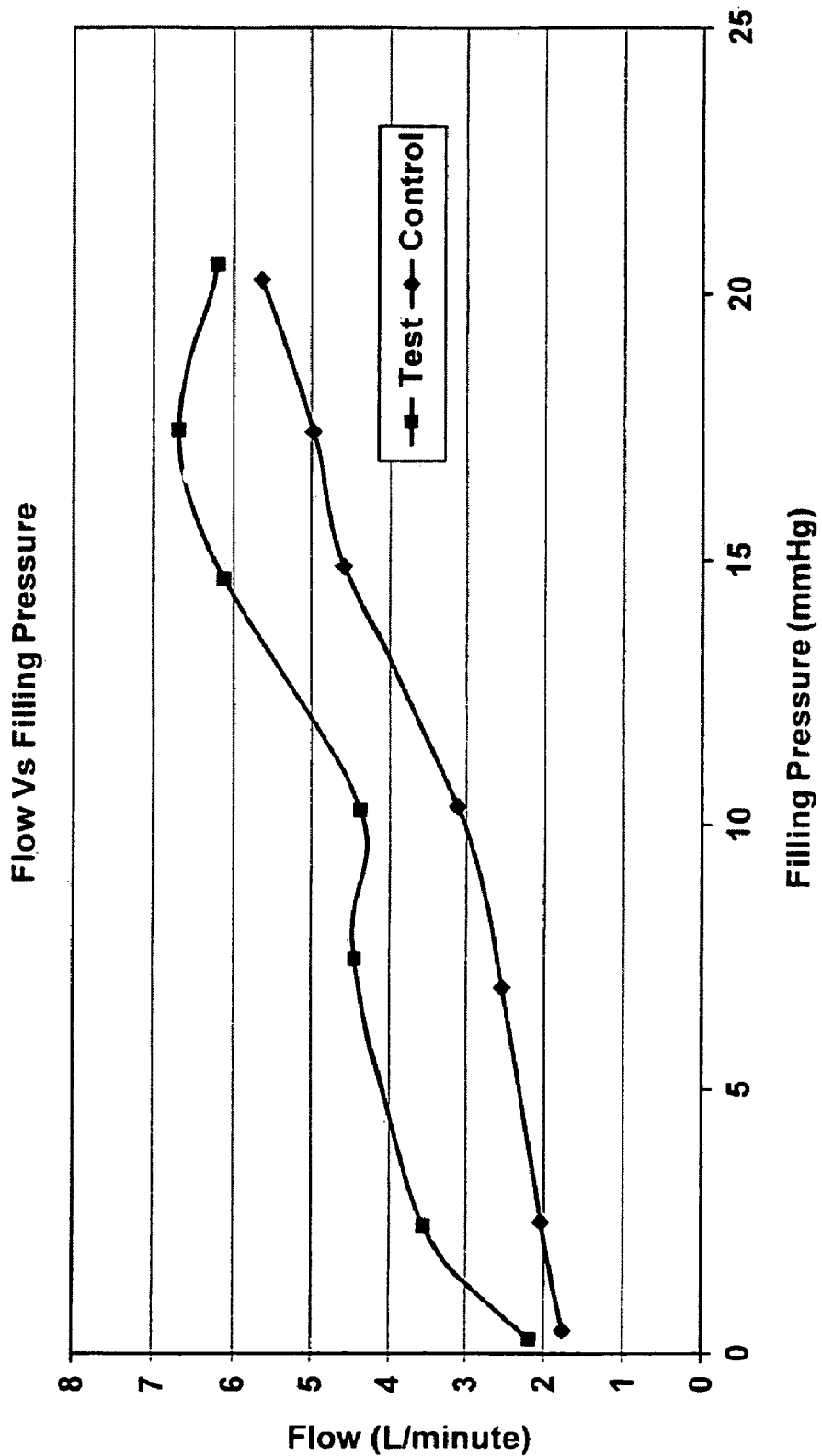
FIG. 22 is a graph comparing the flow performance of a valve and a control valve, each comprised of porcine pericardium. In accordance with the methods of the present invention, the control valve was dehydrated, crimped, sterilized, stored in a fluid-free container for 53 days, and then re-hydrated in water prior to testing.
Figure 23:
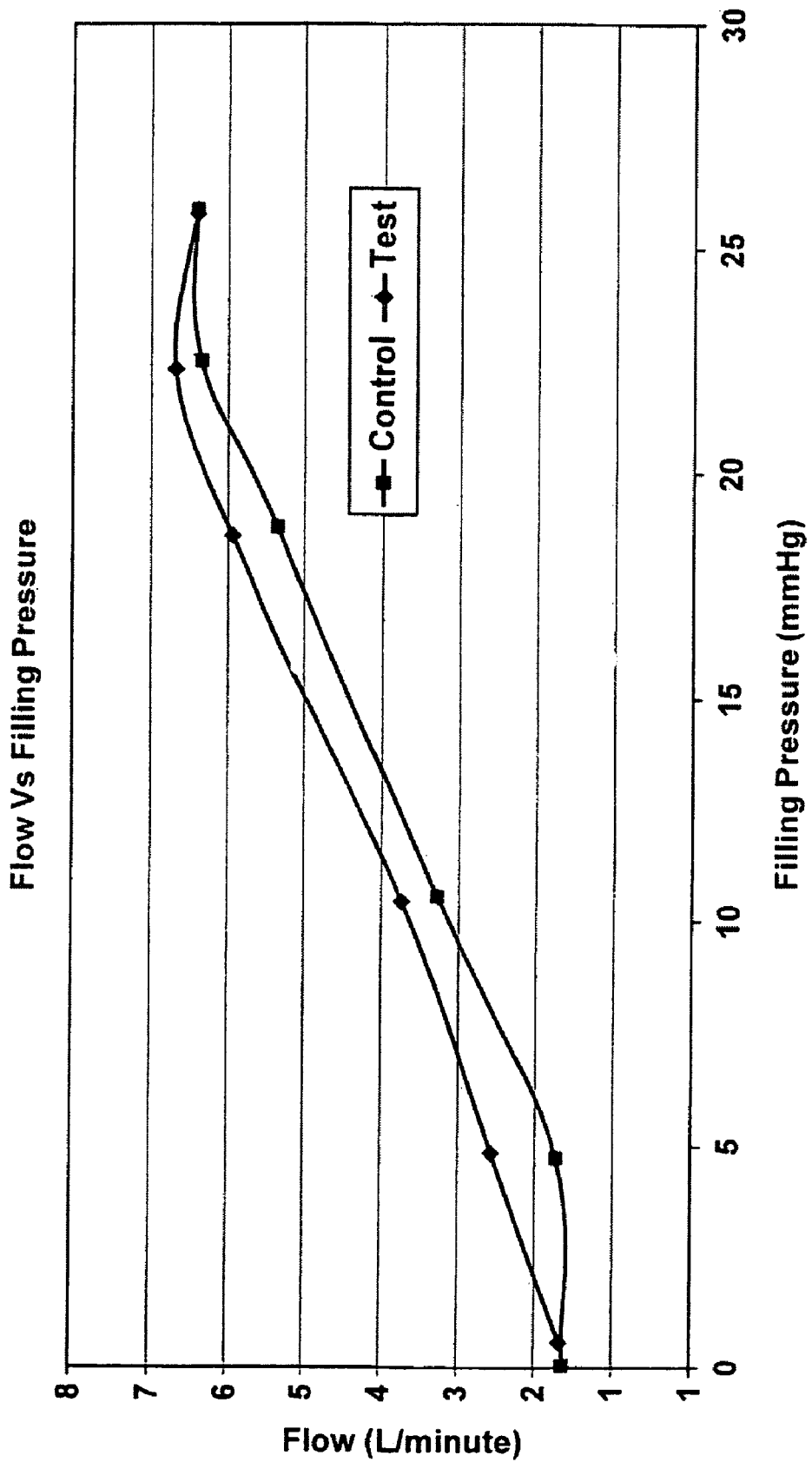
FIG. 23 is a graph comparing the flow performance of a valve and a control valve, each comprised of bovine pericardium. In accordance with the methods of the present invention, the control valve was dehydrated, crimped, sterilized, stored in a fluid-free container for 53 days, and then re-hydrated in water prior to testing.
Figure 24:
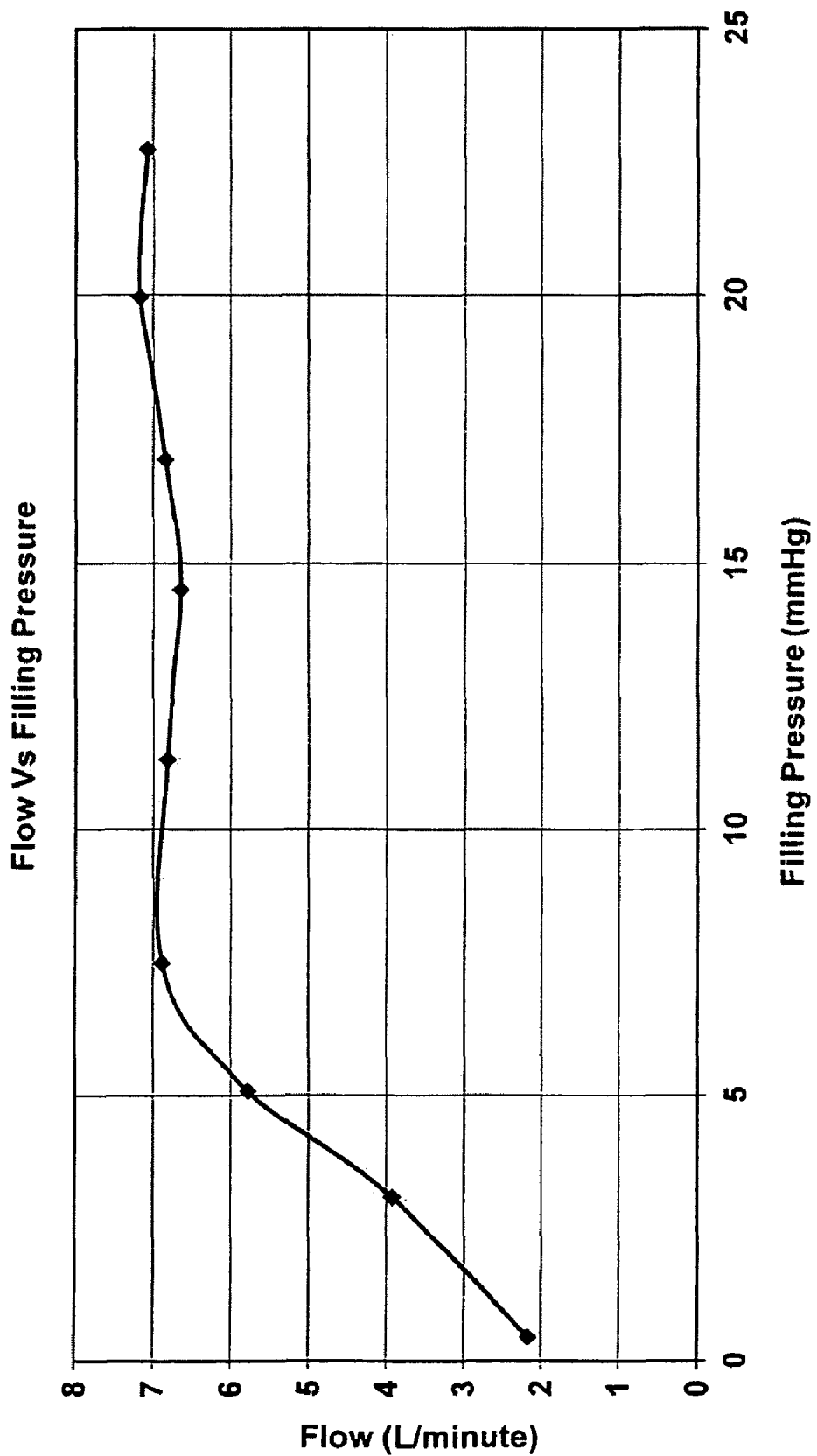
FIG. 24 is a graph depicting the flow performance of a control valve comprised of bovine pericardium.
Figure 25:
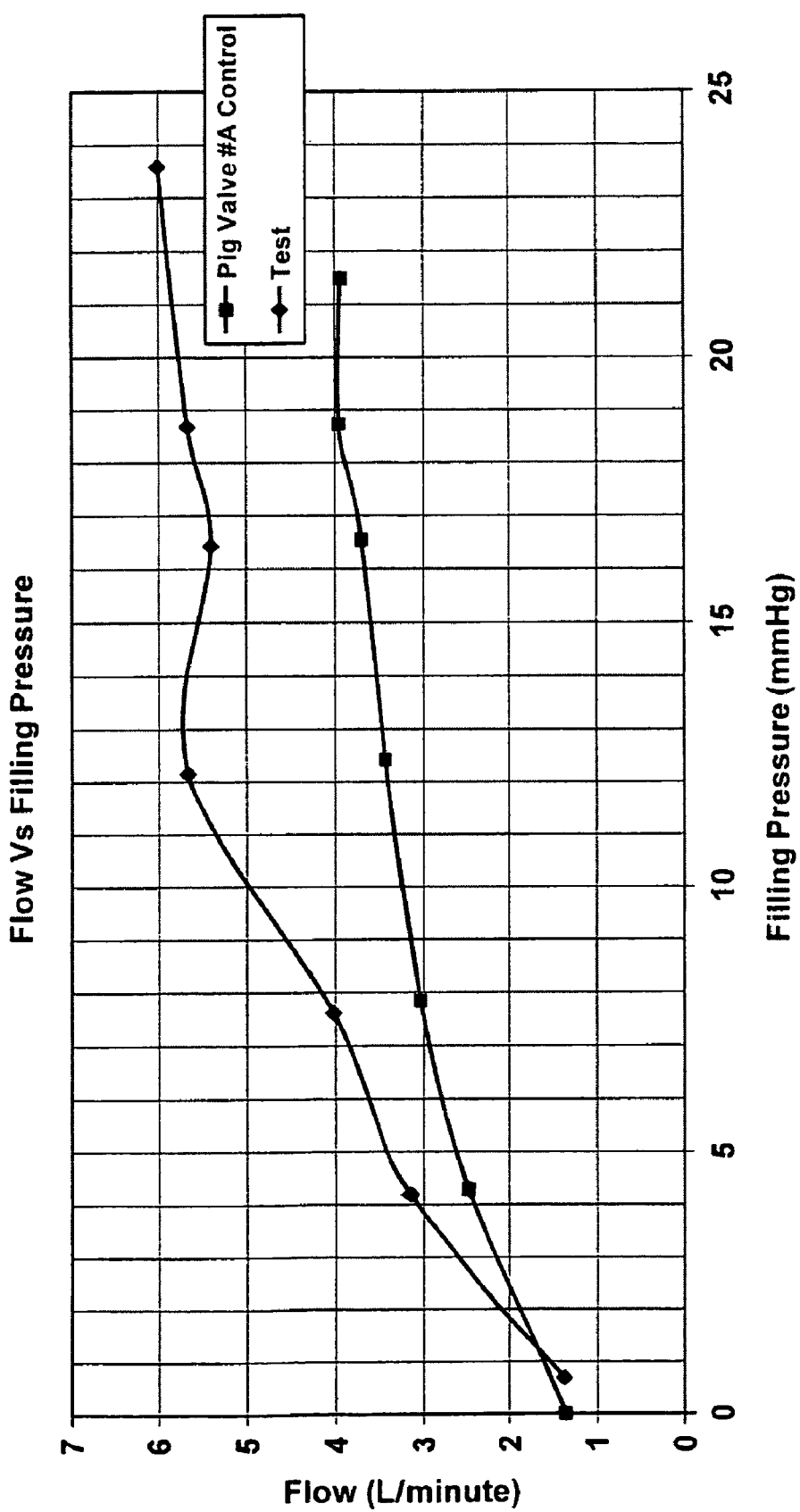
FIG. 25 is a graph comparing the flow performance of a valve and a control valve, each comprised of porcine pericardium. In accordance with the methods of the present invention, the control valve was dehydrated, crimped, sterilized, stored in a fluid-free container for 53 days, and then re-hydrated in water prior to testing.

Another embodiment of the present invention is illustrated in FIG. 20. In FIG. 20, a method $10_b$ is provided for implanting a valve 30 having at least one valve leaflet 36 within the cardiovascular system of a subject. The method $10_b$ is identical to the method 10 illustrated in FIG. 1, except where as described below. As described above, a substantially dehydrated bioprosthetic valve 32 may be prepared at $12_b$ and securely attached to an expandable support member 34 at $16_b$. After forming the substantially dehydrated bioprosthetic valve 32, the substantially dehydrated bioprosthetic valve may be attached to an expandable support member 34 at $16_b$ to form a valve 30, and then exposed to a re-hydrating fluid at 118. The valve 30 may be immersed in the re-hydrating fluid for a time appropriate so that the substantially dehydrated bioprosthetic valve 32 is re-hydrated and obtains (or substantially obtains) its original properties.

As described above, the valve 30 may next be loaded into a delivery catheter 86 as described above. Access to a desired location within the cardiovascular system of a subject may then be obtained. As described above, for example, access to a femoral vein may be obtained so that the valve 30 may be implanted in place of a diseased mitral valve 70. After obtaining access to the cardiovascular system of the subject, the valve 30 may be appropriately placed and expanded at $20_b$ and $22_b$, respectively (as described above). Because the substantially dehydrated bioprosthetic valve 32 is re-hydrated prior to implantation, the substantially dehydrated bioprosthetic valve can function normally immediately upon introduction to the cardiovascular system of the subject.

It should be appreciated that the valve 30 may be rinsed prior to implantation. For example, where the valve 30 is disposed in a delivery catheter 86 and stored in a container essentially free of liquid prior to delivery, the delivery catheter may be rinsed or flushed with a sterile fluid, such as sterile saline or water, before insertion into a subject. Alternatively, the valve 30 may be rinsed while in an expanded configuration in a suitable container 120, for example, crimped into the compressed configuration, and delivered to a subject as described above.

From the above description of the invention, those skilled in the art will perceive improvements, changes and modifications. For example, the substantially dehydrated bioprosthetic valve 32 may be exposed to a re-hydrating or rinsing solution while the valve 30 is disposed within a delivery catheter 86 prior to delivery. Such improvements, changes and modifications within the skill of the art are intended to be covered by the appended claims.

Having described the invention, we claim:

1. A method for implanting a valve having at least one valve leaflet within the cardiovascular system of a subject, said method comprising the steps of:
    preparing a substantially dehydrated bioprosthetic valve comprising the steps of treating a tissue component with an aqueous dimensional stabilizer solution and then substantially dehydrating the tissue component;
    providing an expandable support member having oppositely disposed first and second ends and a main body portion extending between the ends;
    attaching the substantially dehydrated bioprosthetic valve to the expandable support member so that the substantially dehydrated bioprosthetic valve is operably secured within the main body portion of the expandable support member;
    crimping the expandable support member into a compressed configuration; and
    placing the expandable support member at a desired location within the cardiovascular system of the subject.

2. The method of claim 1, wherein said step of placing the expandable support member at a desired location within the cardiovascular system of the subject further comprises the steps of:
    loading the expandable support member into a delivery catheter;
    obtaining access to the desired location;
    delivering the expandable support member to the desired location; and
    expanding the expandable support member into engagement with the cardiovascular tissue at the desired location.

3. The method of claim 1, wherein said step of preparing a substantially dehydrated bioprosthetic valve further comprises the steps of:
    storing the substantially dehydrated bioprosthetic valve in a container that is essentially free of liquid.

4. The method of claim 3 further comprising the step of sterilizing the substantially dehydrated bioprosthetic valve by exposure to one of ethylene oxide gas or ionizing radiation either before or after placement in the container.

5. The method of claim 1, wherein said step of crimping the expandable support member further comprises the step of exposing the substantially dehydrated bioprosthetic valve to a re-hydrating fluid.

6. The method of claim 1, wherein blood re-hydrates the substantially dehydrated bioprosthetic valve before the expandable support member is placed at the desired location.

7. The method of claim 1, wherein blood re-hydrates the substantially dehydrated bioprosthetic valve after the expandable support member is placed at the desired location.

8. The method of claim 1, wherein said step of placing the expandable support member at a desired location within the cardiovascular system of the subject is done percutaneously via the delivery catheter.

9. The method of claim 1, wherein said step of placing the expandable support member at a desired location within cardiovascular system of the subject is done via a minimally invasive, open surgical approach.

10. A method for implanting a valve having at least one valve leaflet within the cardiovascular system of a subject, said method comprising the steps of:
    preparing a substantially dehydrated bioprosthetic valve comprising the steps of treating a tissue component with an aqueous dimensional stabilizer solution and then substantially dehydrating the tissue component;
    providing an expandable support member having oppositely disposed first and second ends and a main body portion extending between the ends;
    attaching the substantially dehydrated bioprosthetic valve to the expandable support member so that the substantially dehydrated bioprosthetic valve is operably secured within the main body portion of the expandable support member;
    crimping the expandable support member into a compressed configuration, followed by
    exposing the substantially dehydrated bioprosthetic valve to a re-hydrating fluid; and
    placing the expandable support member at a desired location within the cardiovascular system of the subject.

11. The method of claim 10, wherein said step of placing the expandable support member at a desired location within the cardiovascular system of the subject further comprises the steps of:
    loading the expandable support member into a delivery catheter;
    obtaining access to the desired location;
    delivering the expandable support member to the desired location; and
    expanding the expandable support member into engagement with the cardiovascular tissue at the desired location.

12. The method of claim 10, wherein said step of preparing a substantially dehydrated bioprosthetic valve further comprises the steps of:
    storing the substantially dehydrated bioprosthetic valve in a container that is essentially free of liquid.

13. The method of claim 12 further comprising the step of sterilizing the substantially dehydrated bioprosthetic valve by exposure to one of ethylene oxide gas or ionizing radiation either before or after placement in the container.

14. The method of claim 10, wherein said step of crimping the expandable support member further comprises the step of exposing the substantially dehydrated bioprosthetic valve to a re-hydrating fluid.

15. The method of claim 10, wherein said step of placing the expandable support member at a desired location within the cardiovascular system of the subject is done percutaneously via the delivery catheter.

16. The method of claim 10, wherein said step of placing the expandable support member at a desired location within the cardiovascular system of the subject is done via a minimally invasive, open surgical approach.

17. A method for implanting a valve having at least one valve leaflet within the cardiovascular system of a subject, said method comprising the steps of:
   preparing a substantially dehydrated bioprosthetic valve comprising the steps of treating a tissue component with an aqueous dimensional stabilizer solution and then substantially dehydrating the tissue component;
   providing an expandable support member having oppositely disposed first and second ends and a main body portion extending between the ends;
   attaching the substantially dehydrated bioprosthetic valve to the expandable support member so that the substantially dehydrated bioprosthetic valve is operably secured within the main body portion of the expandable support member;
   exposing the substantially dehydrated bioprosthetic valve to a re-hydrating fluid, followed by
   crimping the expandable support member into a compressed configuration; and
   placing the expandable support member at a desired location within the cardiovascular system of the subject.

18. The method of claim 17, wherein said step of placing the expandable support member at a desired location within the cardiovascular system of the subject further comprises the steps of:
   loading the expandable support member into a delivery catheter;
   obtaining access to the desired location;
   delivering the expandable support member to the desired location; and
   expanding the expandable support member into engagement with the cardiovascular tissue at the desired location.

19. The method of claim 17, wherein said step of preparing a substantially dehydrated bioprosthetic valve further comprises the steps of:
   storing the substantially dehydrated bioprosthetic valve in a container that is essentially free of liquid.

20. The method of claim 19 further comprising the step of sterilizing the substantially dehydrated bioprosthetic valve by exposure to one of ethylene oxide gas or ionizing radiation either before or after placement in the container.

21. The method of claim 17, wherein said step of placing the expandable support member at a desired location within the cardiovascular system of the subject is done percutaneously via the delivery catheter.

22. The method of claim 17, wherein said step of placing the expandable support member at a desired location within the cardiovascular system of the subject is done via a minimally invasive, open surgical approach.

* * * * *